United States Patent
Zhao et al.

(10) Patent No.: US 11,447,606 B2
(45) Date of Patent: Sep. 20, 2022

(54) FLUORESCENT POROUS ORGANIC NANOSHEETS FOR CHEMICAL SENSING

(71) Applicant: NATIONAL UNIVERSITY OF SINGAPORE, Singapore (SG)

(72) Inventors: Dan Zhao, Singapore (SG); Jinqiao Dong, Singapore (SG)

(73) Assignee: National University of Singapore, Singapore (SG)

( * ) Notice: Subject to any disclaimer, the term of this patent is extended or adjusted under 35 U.S.C. 154(b) by 303 days.

(21) Appl. No.: 16/495,645

(22) PCT Filed: Mar. 21, 2018

(86) PCT No.: PCT/SG2018/050126
§ 371 (c)(1),
(2) Date: Sep. 19, 2019

(87) PCT Pub. No.: WO2018/174823
PCT Pub. Date: Sep. 27, 2018

(65) Prior Publication Data
US 2020/0024406 A1    Jan. 23, 2020

(30) Foreign Application Priority Data
Mar. 22, 2017   (SG) .......................... 10201702327X

(51) Int. Cl.
G01N 21/64 (2006.01)
G01N 33/22 (2006.01)
C08G 83/00 (2006.01)
C08J 5/18 (2006.01)
G01N 33/00 (2006.01)
G01N 33/20 (2019.01)

(52) U.S. Cl.
CPC .............. *C08G 83/003* (2013.01); *C08J 5/18* (2013.01); *G01N 21/64* (2013.01); *C08J 2387/00* (2013.01); *G01N 33/0004* (2013.01); *G01N 33/20* (2013.01); *G01N 33/227* (2013.01); *G01N 2201/08* (2013.01)

(58) Field of Classification Search
CPC ................ B01J 20/262; B01J 20/28035; B01J 20/28057; B01J 20/28073; B01J 20/28083; C08G 2261/132; C08G 2261/3422; C08G 2261/415; C08G 2261/94; C08G 61/02; C08G 83/003; C08J 2387/00; C08J 5/18; G01N 21/64; G01N 2201/08; G01N 33/0004; G01N 33/20; G01N 33/227; Y10T 436/142222; Y10T 436/17; Y10T 436/21; Y10T 436/212
USPC ......... 436/93, 106, 139, 140, 164, 166, 172; 422/82.05, 82.08
See application file for complete search history.

(56) References Cited

U.S. PATENT DOCUMENTS

| | | | | |
|---|---|---|---|---|
| 7,700,366 B2* | 4/2010 | Swager | ................. | C08G 61/06 436/172 |
| 8,367,419 B2* | 2/2013 | Li | ........................... | C07F 3/003 436/107 |
| 8,765,483 B2* | 7/2014 | Lei | ....................... | G01N 31/227 436/110 |
| 2011/0057116 A1* | 3/2011 | Trogler | .................. | C09K 11/06 250/458.1 |
| 2021/0088449 A1* | 3/2021 | Makkad | ................ | C08F 112/08 |

FOREIGN PATENT DOCUMENTS

CN           102442873          5/2012

OTHER PUBLICATIONS

Rathore et al. Organic Letters, vol. 6, No. 11, 2004, pp. 1689-1692.*
Dong et al. Journal of the American Chemical Society, vol. 140, Feb. 28, 2018, pp. 4035-4046.*
Chang et al., Hexaphenylbenzene-Based, pi-Conjugated Snowflakeshaped Luminophores:Tunable Aggregation-Induced Emission Effect and Piezofluorochromism, Chemistry—A European Journal, vol. 21, No. 23, Apr. 2015, pp. 1-8.
Chen et al., Porous Organic Polymers Based on Propeller-Like Hexaphenylbenzene Building Units, Macromolecules, vol. 44, No. 14, Jun. 30, 2011, pp. 5573-5577.
Dong et al., Fluorescent Porous Organic Frameworks Containing Molecular Rotors for Size-Selective Recognition, Chemistry of Materials, vol. 28, No. 21, Oct. 2016, pp. 7889-7897.
International Application No. PCT/SG2018/050126, International Search Report and Written Opinion dated Jun. 4, 2018, 9 pages.
(Continued)

*Primary Examiner* — Maureen Wallenhorst
(74) *Attorney, Agent, or Firm* — Kilpatrick Townsend & Stockton LLP

(57) ABSTRACT

Disclosed herein is a porous polymeric material having a repeating unit according to Formula (I) or (IV), wherein each of A and E has a π conjugated system and each of X and G contain a flexible tetraphenylethylene (TPE) group. Also disclosed herein are fluorescent chemical sensors or biosensors or environmental monitoring assays or nanosheets or composite materials that include the polymer, and a method of detecting a volatile organic chemical or a metal ion in solution phase.

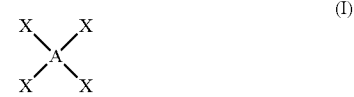

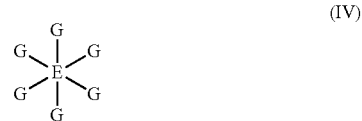

11 Claims, 14 Drawing Sheets

(56) References Cited

OTHER PUBLICATIONS

Figure 1:
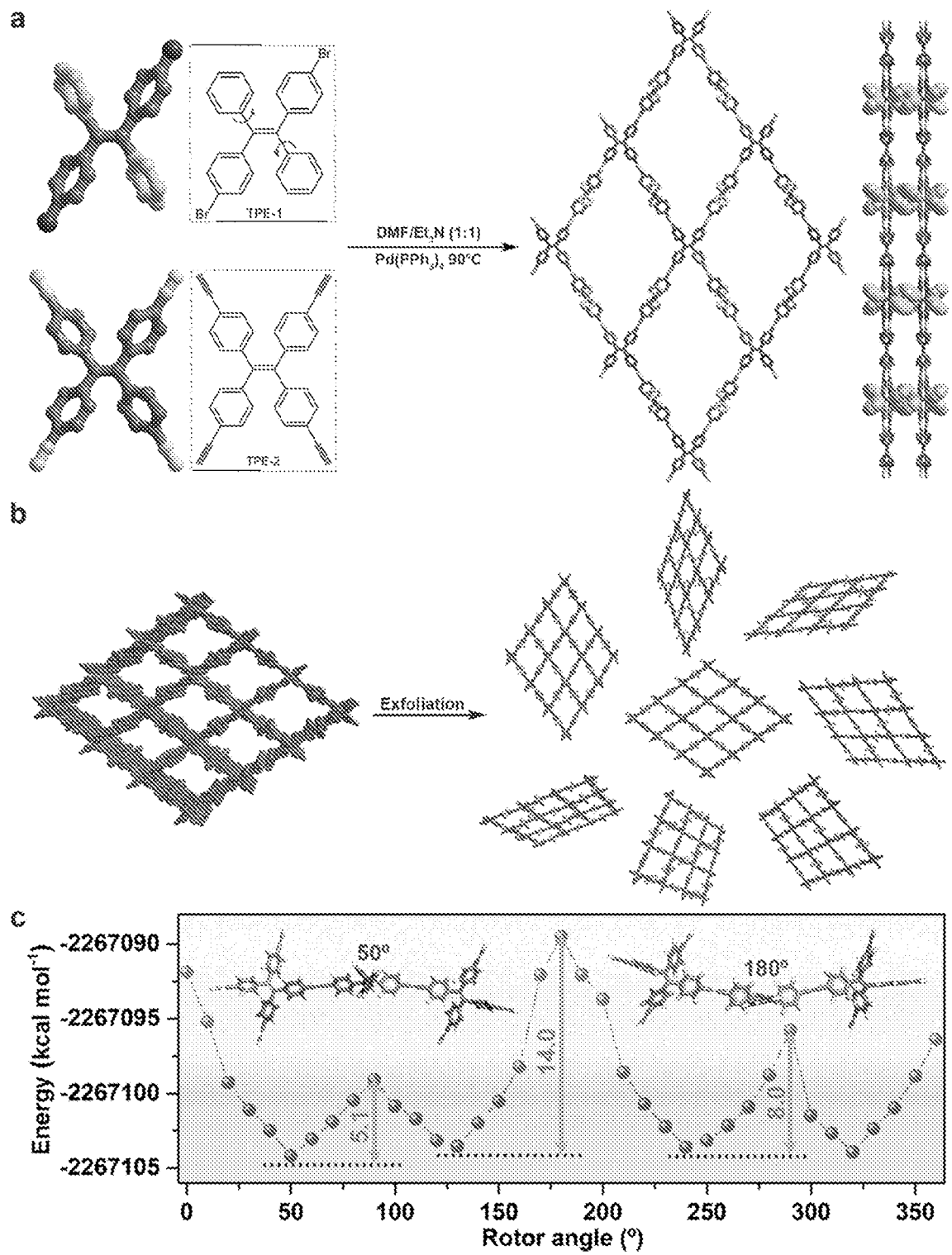

Thompson et al., Substituent Effects on the Gas Sorption and Selectivity Properties of Hexaphenylbenzene and Hexabenzocoronene Based Porous Polymers, Macromolecules, vol. 47, No. 24, Dec. 3, 2014, pp. 8645-8652.

Yuan et al., Nanofibrous and Graphene-Templated Conjugated Microporous Polymer Materials for Flexible Chemosensors and Supercapacitors, Chemistry of Materials, vol. 27, No. 21, Oct. 16, 2015, pp. 7403-7411.

European Application No. 18771856.4, Extended European Search Report, dated Nov. 25, 2020, 9 pages.

Chinese Application No. CN201880033362.7, Office Action dated Dec. 10, 2021, 17 pages.

* cited by examiner

FLUORESCENT POROUS ORGANIC NANOSHEETS FOR CHEMICAL SENSING

FIELD OF INVENTION

The current invention relates to polymers or porous organic nanosheets that can exhibit fluorescence. The present invention further relates to the preparation and application of said polymers, particularly in the detection of volatile organic compounds, $Fe^{3+}$ ions and/or acenaphthylene.

BACKGROUND

The listing or discussion of a prior-published document in this specification should not necessarily be taken as an acknowledgement that the document is part of the state of the art or is common general knowledge.

There is a great market potential for the facile detection of trace amount of organic vapours in the areas of environmental monitoring and homeland security. Based on a new report released recently by the World Health Organization (WHO), 7 million people died in 2012 as a result of air pollution exposure. This number equals to ⅛ of the total number of deaths globally, confirming that air pollution is currently the world's largest single environmental health risk. Volatile organic compounds (VOCs) such as aliphatic hydrocarbons, chlorocarbons, formaldehyde, benzene, etc., are major sources of air pollution. Therefore, there is an urgent need to develop sensors that can detect VOCs to monitor air quality and save lives. It has been estimated that the market of air quality monitoring will be worth USD 5.64 billion by 2021. In addition, given the prevailing threat of global terrorism, the detection of trace amounts of explosives, such as nitro-containing explosive compounds, has become an urgent need and this market is expected to be worth USD 6.12 billion by 2020.

Most methods of detecting organic vapour or explosives, such as air monitoring at particular areas and explosive detection at airports, require sampling and on the spot decision making using portable devices. Currently, the most widely used technologies for organic vapour detection include gas chromatography (GC), mass spectroscopy (MS), and ion mobility spectrometry (IMS). However, they are too complicated and expensive to be used in portable devices. Therefore, there is a need for low-cost on-site sensors for use in portable devices that combine the properties of high sensitivity, broad selectivity and easy operation.

Fluorescence is the emission of light by a substance that has absorbed light or other electromagnetic radiation. Because of its versatility and high sensitivity toward external stimuli, fluorescence has been widely used in various sensing applications including the sensing of organic vapours. Portable devices can be easily fabricated by integrating suitable fluorescent materials with optical fiber sensors without complex circuit design. Considering that the mean concentration of organic vapours for the applications of air monitoring and explosive detection is very low (below 50 µg/m³), the ideal fluorescent materials should be porous so as to pre-concentrate organic vapours through physisorption to enable high detection sensitivity. In addition, 2D nanosheet morphology is preferred for the fluorescent materials to be processed into coating or film morphology suitable for device fabrication.

Since the discovery of mechanically-exfoliated graphene, the recent decade has witnessed the development of ultrathin two-dimensional (2D) nanomaterials. These 2D materials, containing several layers or even a monolayer, exhibit promising properties in chemical sensing or biosensing applications. Compared to 3D bulk materials, ultrathin 2D nanomaterials possess more accessible active sites on their surface, leading to enhanced sensing sensitivities. Although much progress on fluorescent ultrathin 2D nanosheets has been achieved, there are still two issues that need to be solved: (1) the fluorescent emission (quantum yield) of 2D nanosheets needs to be improved; and (2) the tendency of ultrathin 2D nanosheets to re-stack into bulk materials needs to be mitigated. Therefore, there remains a need for new 2D nanomaterials that can overcome these two problems.

SUMMARY OF INVENTION

The invention provides new polymers, or porous organic nanosheets (PONs), that exhibit fluorescence emission. They may be used to detect explosives (e.g. nitrobenzene). In certain cases, the materials disclosed herein may be suitable for use in chemical sensors for detection of $Fe^{3+}$ ions and/or at least one VOC, such as in a chemical sensor for detection of acenaphthylene.

Aspects and embodiments of the invention will now be described with reference to the following numbered clauses.

1. A polymer having a repeating unit according to Formula (I):

wherein A represents a central portion of the polymeric repeating unit and is represented by formula (II):

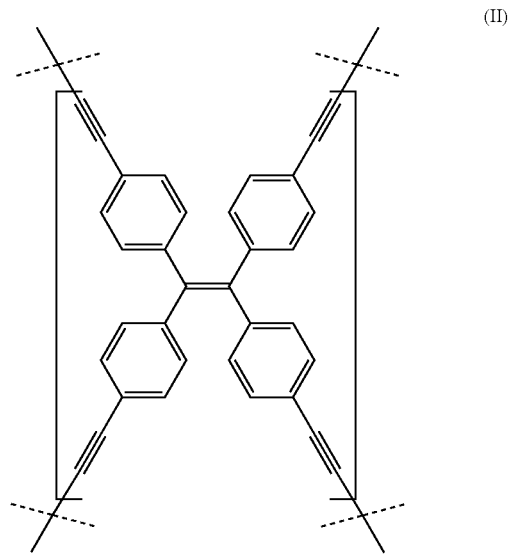

where the dotted lines relate to the points of attachment to X; and wherein each X represents a peripheral portion of the polymeric repeating unit and is represented by formula (III):

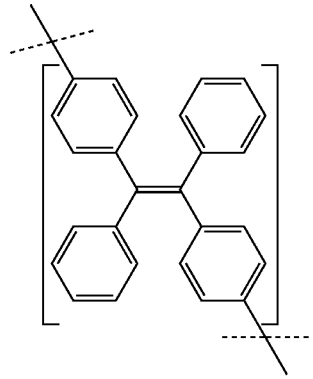

where the dotted lines relate to the points of attachment to unit A, or salts and solvates thereof.

2. The polymer according to Clause 1, wherein the compound of formula (I) is provided as a bulk polymer, optionally wherein the bulk polymer further has one or more of the following properties:
   (a) a BET surface area of from 250 to 500 $m^2\ g^{-1}$ (e.g. 335 $m^2\ g^{-1}$);
   (b) a total pore volume of from 0.3 to 0.5 $cm^3\ g^{-1}$ (e.g. 0.378 $cm^3\ g^{-1}$); and
   (c) micropores having a diameter of from 5 to 17 Å (e.g. 14 Å) and macropores having a diameter of from 25 to 35 Å (e.g. 28 Å).

3. The polymer according to Clause 1, wherein the compound of formula (I) is provided as a nanosheet, where the nanosheets have from one to four layers (e.g. one layer) of the polymer of formula (I).

4. The polymer according to Clause 3, wherein the nanosheets have one or more of the following properties:
   (a) a BET surface area of from 90 to 200 $m^2\ g^{-1}$ (e.g. 92 $m^2\ g^{-1}$ in acetonitrile, 100 $m^2\ g^{-1}$ in acetone, or 162 $m^2\ g^{-1}$ in ethanol);
   (b) a total pore volume of from 0.1 to 0.35 $cm^3\ g^{-1}$ (e.g. 0.13 $cm^3\ g^{-1}$ in acetone or acetonitrile, or 0.20 $cm^3\ g^{-1}$ in ethanol);
   (c) pores having a diameter of from 5 to 17 Å (e.g. 14 Å);
   (d) a sheet size of from 400 to 800 nm when measured in an organic solvent by dynamic light scattering (e.g. 404 nm when measured in acetonitrile, 529 nm when measured in acetone, or 657 nm when measured in ethanol); and
   (e) a thickness of from 2 to 5 nm.

5. Preparation of a polymer of formula (I) as described in Clause 1 comprising reaction of a compound of formula (VI):

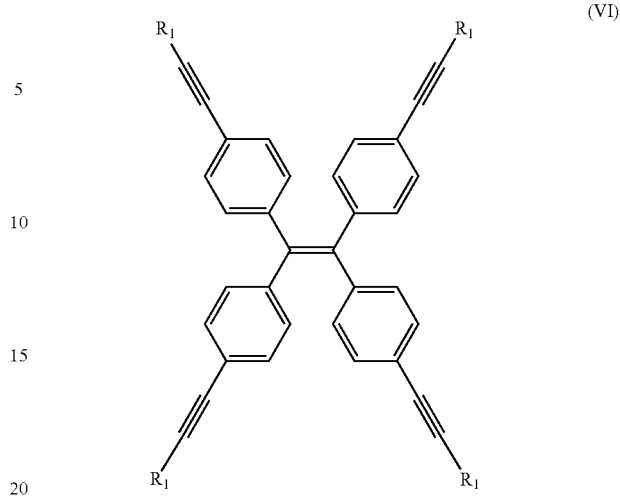

where $R_1$ represents H, with a compound of formula (VII):

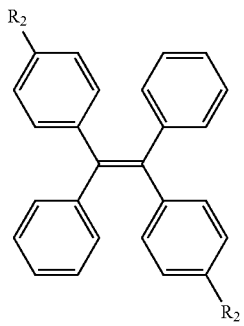

where $R_2$ represents halo.

6. The preparation of Clause 5, wherein a bulk polymeric form of the polymer of formula (I) is formed using the process of Clause 5 is further exfoliated to provide nanosheets of the polymer of formula (I), where the nanosheets have from one to four layers (e.g. one layer) of the polymer of formula (I).

7. The preparation of Clause 6, wherein the resulting nanosheets of the polymer of formula (I) are placed into a solvent comprising a polymeric material without electron withdrawing group moieties and/or aromatic or heteroaromatic rings and solvent cast to form a mixed matrix membrane material, optionally wherein the polymeric material without electron withdrawing group moieties and/or aromatic or heteroaromatic rings is polyethylene imine.

8. A composite material in the form of a mixed matrix membrane material comprising a polymer of formula (I) according to any one of Clauses 1 to 4 dispersed within a polymeric matrix material formed from a polymer without electron withdrawing group moieties and/or aromatic or heteroaromatic rings, optionally wherein the polymeric material without electron withdrawing group moieties and/or aromatic or heteroaromatic rings is polyethylene imine.

9. A chemical sensor comprising a polymer of formula (I), as described in any one of Clauses 1 to 4 or a composite material of Clause 8, optionally wherein the polymer is provided as a bulk polymer or as a nanosheet, where the nanosheets have from one to four layers (e.g. one layer) of the polymer.

10. A sensor device comprising an optical fiber and a polymer of formula (I) as described in any one of Clauses 1 to 4 or a composite material of Clause 8, optionally wherein the polymer is provided as a bulk polymer or as a nanosheet, where the nanosheets have from one to four layers (e.g. one layer) of the polymer.

11. A method of detecting a volatile organic compound and/or explosive compounds and/or a metal ion with a chemical sensor as described in Clause 9 or a sensor device as described in Clause 10, wherein the sensor is exposed to an analyte and detects volatile organic compounds and/or explosive compounds and/or a metal ion, wherein the sensor detects volatile organic compounds by turn-on fluorescence or the sensor detects explosive compounds or a metal ion by turn-off fluorescence in a quantitative manner or in a qualitative manner, optionally wherein:

(a) the at least one volatile organic compound is selected from one or more of the group consisting of dichloromethane, chloroform, tetrahydrofuran, n-hexane, cyclohexane, benzene, naphthalene, phenathrene, toluene, o-xylene, m-xylene, p-xylene, 1,4-diisopropylbenzene, aniline and mixtures thereof; and/or (b) the explosive compound is an organic compound comprising one or more nitro groups, such as nitrobenzene, nitromethane, 2-nitrotoluene and 2,4,6-trinitrophenol, or mixtures thereof; and/or (c) the metal ion is selected from one or more of $Cu^{2+}$, $Co^{2+}$, $Mn^{2+}$ and $Fe^{3+}$ (e.g. the metal ion is $Fe^{3+}$).

12. A polymer having a repeating unit according to Formula (IV):

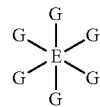

(IV)

wherein E represents a central portion of the polymeric repeating unit and is represented by formula (V):

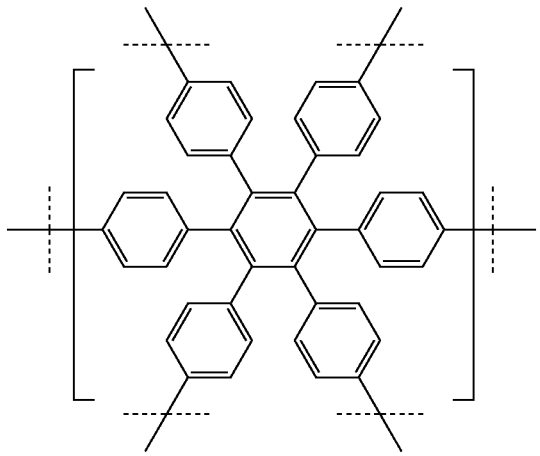

(V)

where the dotted lines relate to the points of attachment to G; and wherein each G represents a peripheral portion of the polymeric repeating unit and is represented by formula (III):

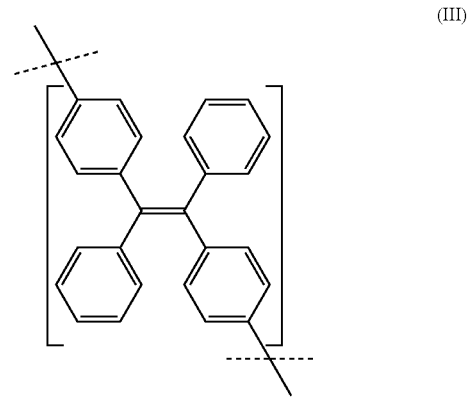

(III)

where the dotted lines relate to the points of attachment to unit A, or salts and solvates thereof.

13. The polymer according to Clause 12, wherein the compound of formula (IV) is provided as a bulk polymer, optionally wherein the bulk polymer further has one or more of the following properties:

(a) a BET surface area of from 450 to 750 $m^2$ $g^{-1}$ (e.g. 623 $m^2$ $g^{-1}$);
(b) a total pore volume of from 0.5 to 0.9 $cm^3$ $g^{-1}$ (e.g. 0.69 $cm^3$ $g^{-1}$); and
(c) pores having a diameter of from 5 to 17 Å (e.g. 12.6 Å).

14. The polymer according to Clause 12, wherein the compound of formula (IV) is provided as a nanosheet, where the nanosheets have from one to four layers (e.g. one layer) of the polymer of formula (I), optionally wherein the nanosheets have one or more of the following properties:

(a) a BET surface area of from 150 to 300 $m^2$ $g^{-1}$ (e.g. 184 $m^2$ $g^{-1}$ as measured in acetonitrile);
(b) a sheet size of from 2 to 20 μm (e.g. 4 μm) when measured in an organic solvent by dynamic light scattering; and
(c) a thickness of from 2 to 5 nm (e.g. 3 nm).

15. Preparation of a polymer of formula (IV) as described in any one of Clauses 12 to 14, comprising reaction of a compound of formula (VIII):

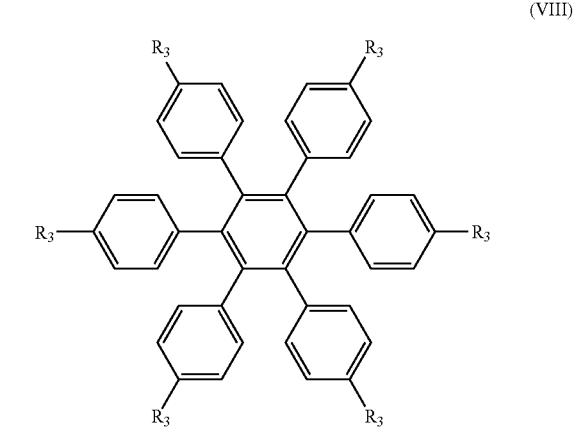

(VIII)

where R₃ represents halo, with a compound of formula (IX):

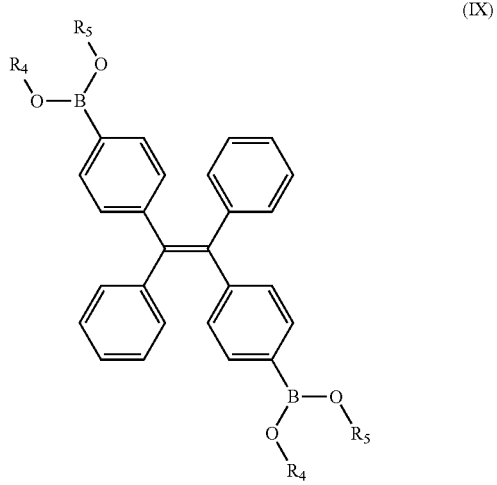

wherein $R_4$ and $R_5$ independently represent $C_{1-6}$ alkyl, or $R_4$ and $R_5$ together with the boron and oxygen atoms to which they are attached form a 5- to 6-membered ring (e.g. a 5-membered ring), which latter two groups are unsubstituted or are substituted with from one to four substituents (e.g. four) selected from $C_{1-6}$ alkyl (e.g. methyl).

16. The preparation of Clause 15, wherein a bulk polymeric form of the polymer of formula (IV) is formed using the process of Clause 15 is further exfoliated to provide nanosheets of the polymer of formula (IV), where the nanosheets have from one to four layers (e.g. one layer) of the polymer of formula (IV).

17. A chemical sensor comprising a polymer of formula (IV) as described in any one of Clauses 12 to 14, optionally wherein the polymer is provided as a bulk polymer or as a nanosheet, where the nanosheets have from one to four layers (e.g. one layer) of the polymer.

18. A sensor device comprising an optical fiber and a polymer of formula (IV), as described in any one of Clauses 12 to 14, optionally wherein the polymer is provided as a bulk polymer or as a nanosheet, where the nanosheets have from one to four layers (e.g. one layer) of the polymer.

19. A method of detecting a volatile organic compound and/or an explosive compound and/or a polycyclic aromatic hydrocarbon with a chemical sensor as described in Clause 17 or a sensor device as described in Clause 18, wherein the sensor is exposed to an analyte and detects volatile organic compounds and/or explosive compounds, wherein the sensor detects volatile organic compounds by turn-on fluorescence or the sensor detects explosive compounds by turn-off fluorescence in a quantitative manner or in a qualitative manner, optionally wherein:
(a) the at least one volatile organic compound is selected from one or more of the group consisting of dichloromethane, chloroform, tetrahydrofuran, n-hexane, cyclohexane, benzene, toluene, o-xylene, m-xylene, p-xylene, 1,4-diisopropylbenzene, and aniline; and/or
(b) the explosive compound is an organic compound comprising one or more nitro groups, such as nitrobenzene, nitromethane, 2-nitrotoluene and 2,4,6-trinitrophenol; and/or
(c) the polycyclic aromatic hydrocarbon is selected from one or more of the group consisting of a fullerene (e.g. $C_{60}$ or, more particularly, $C_{70}$), acenapthylene, pyrene, phenanthrene, fluorene, triphenylene, chrysene, naphthalene, and indene (e.g. the polycyclic aromatic hydrocarbon is selected from one or more of the group consisting of a fullerene, acenapthylene, pyrene, phenanthrene, fluorene, and triphenylene, such as $C_{70}$ and/or acenapthylene and/or pyrene).

DRAWINGS

FIG. 1. Design and synthesis of NUS-24 nanosheets. (a) Synthetic route of NUS-24 bulk powder by Sonogashira-Hagihara coupling reactions. (b) The schematic diagram for the exfoliation of NUS-24 from bulk layered material to 2D nanosheets. The phenyl rings not tied into the backbone of the polymeric/oligomeric may act as dynamic TPE rotors whose motion is liberated after exfoliation. (c) Theoretical calculations of energy barrier of TPE rotors in the constructed models.

Figure 2:
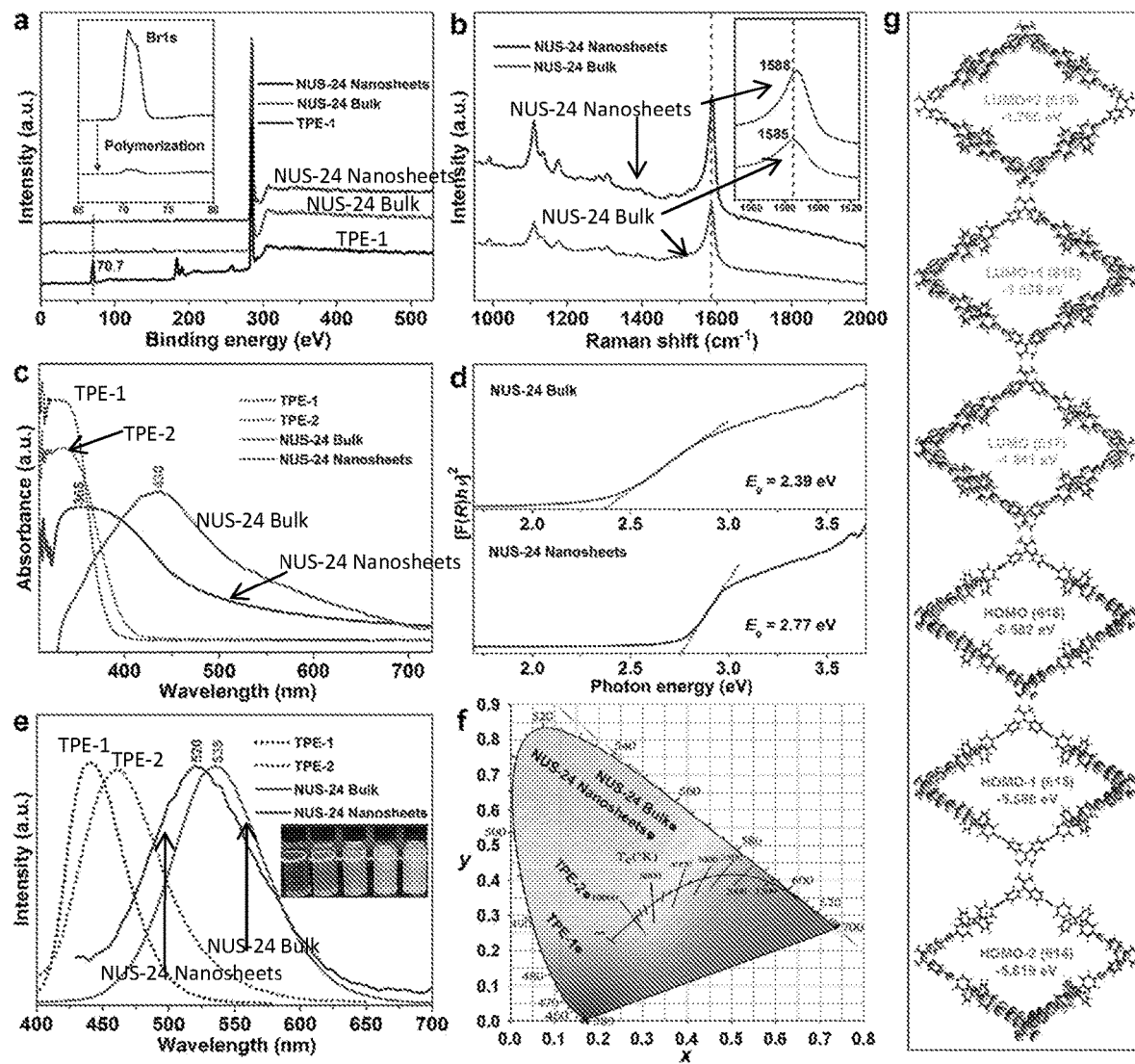

FIG. 2. Spectroscopic characterization of NUS-24 nanosheets. (a) XPS spectra of TPE-1, bulk powder and nanosheets of NUS-24. (b) Raman spectra of bulk powder and nanosheets of NUS-24. (c) UV-Vis spectra of TPE linkers, bulk powder and nanosheets of NUS-24 in acetone solution. (d) Optical band gaps ($E_g$) of bulk powder and nanosheets of NUS-24 in solid state by diffuse reflectance. (e) Fluorescence emission spectra of TPE linkers, bulk powder and nanosheets of NUS-24 in acetone solution (Inset: fluorescence photographs of nanosheets solution with different concentrations in acetone. $\lambda_{ex}$=365 nm). (f) CIE coordinates of emission colour of TPE-1, TPE-2, bulk powder and nanosheets of NUS-24. (g) The frontier molecular orbital distributions of NUS-24 fragment by DFT calculations.

Figure 3:
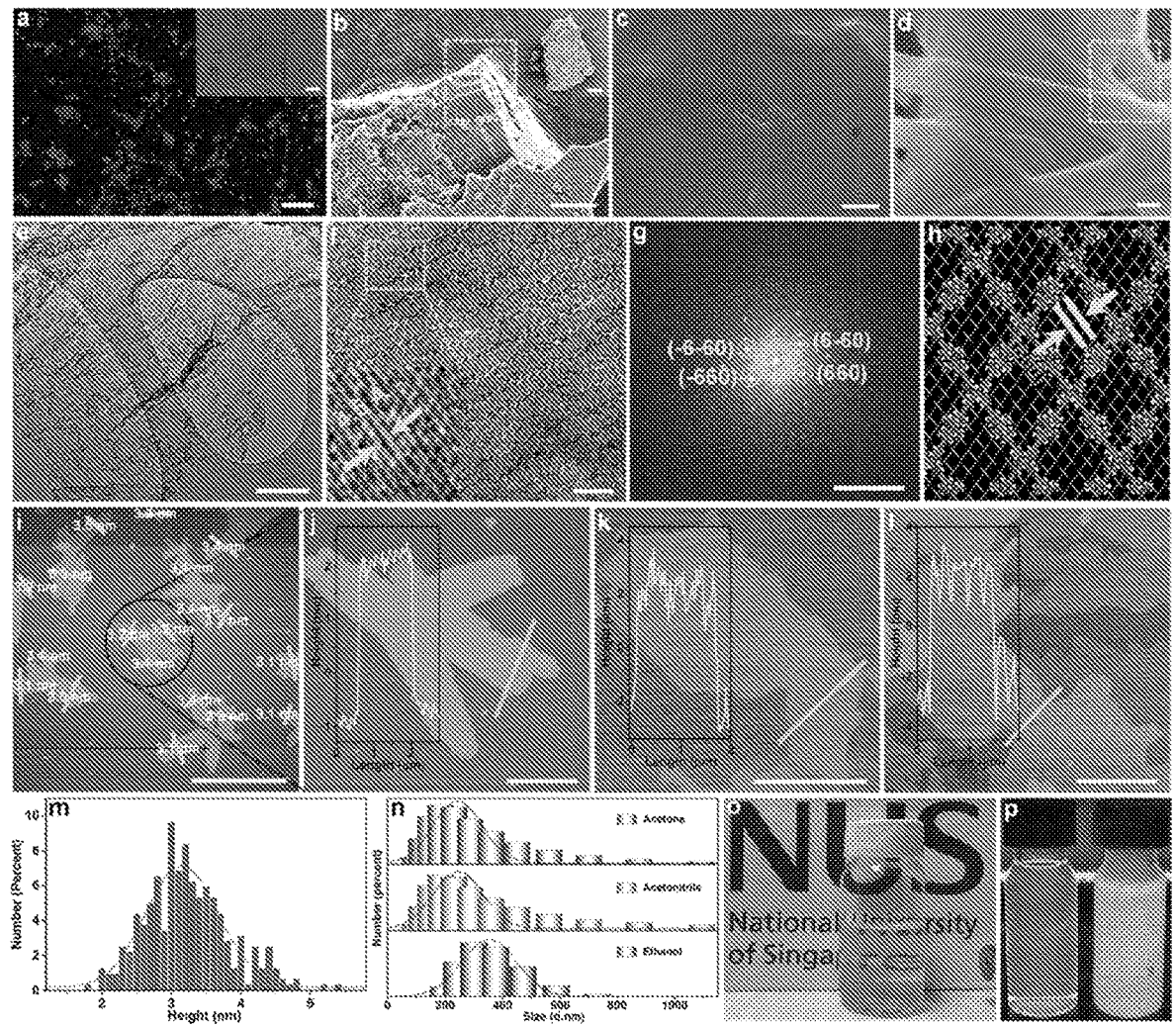

FIG. 3. Morphology characterization of NUS-24 nanosheets. (a) Fluorescence photograph of NUS-24 bulk powder (Scale bar, 3 mm. $\lambda_{ex}$=365 nm). Inset of a, Corresponding optical photograph (Scale bar, 3 mm). (b) FE-SEM image of NUS-24 bulk powder (Scale bar, 10 μm. Scale bar of inset of b, 30 μm). (c,d) d FE-SEM images of NUS-24 nanosheets deposited on AAO substrate (Scale bar, 500 nm in c and 200 nm in d). The circulated rectangular areas indicate the 2D layered structure of NUS-24. (e) TEM image of NUS-24 nanosheets (Scale bar, 200 nm). (f) HR-TEM image of NUS-24 nanosheets featuring the planar lattice structure (Scale bar, 5 nm. Inset: the lattice distance). (g) The Fast Fourier Transformation of f (Scale bar, 5 1/nm). (h) The lattice structure from (660) plane of the optimized NUS-24 crystal structure. (i-l) AFM images of NUS-24 nanosheets dispersed in acetone (i, j), acetonitrile (k), or ethanol (l) (Scale bar, 10 μm in i and 2 μm in j-l. Inset: the height of AFM image for selective area). (m) The statistical height distribution of NUS-24 nanosheets based on 322 AFM measurements. (n) The DLS results of NUS-24 nanosheets in different solutions. (o) The optical photograph of NUS-24 nanosheets in acetone solution indicating strong Tyndall effect. (p) The fluorescent photograph of NUS-24 nanosheets in acetone solution at 298 K (left, solution state) and 77 K (right, solidified state) ($\lambda_{ex}$=365 nm).

Figure 4:
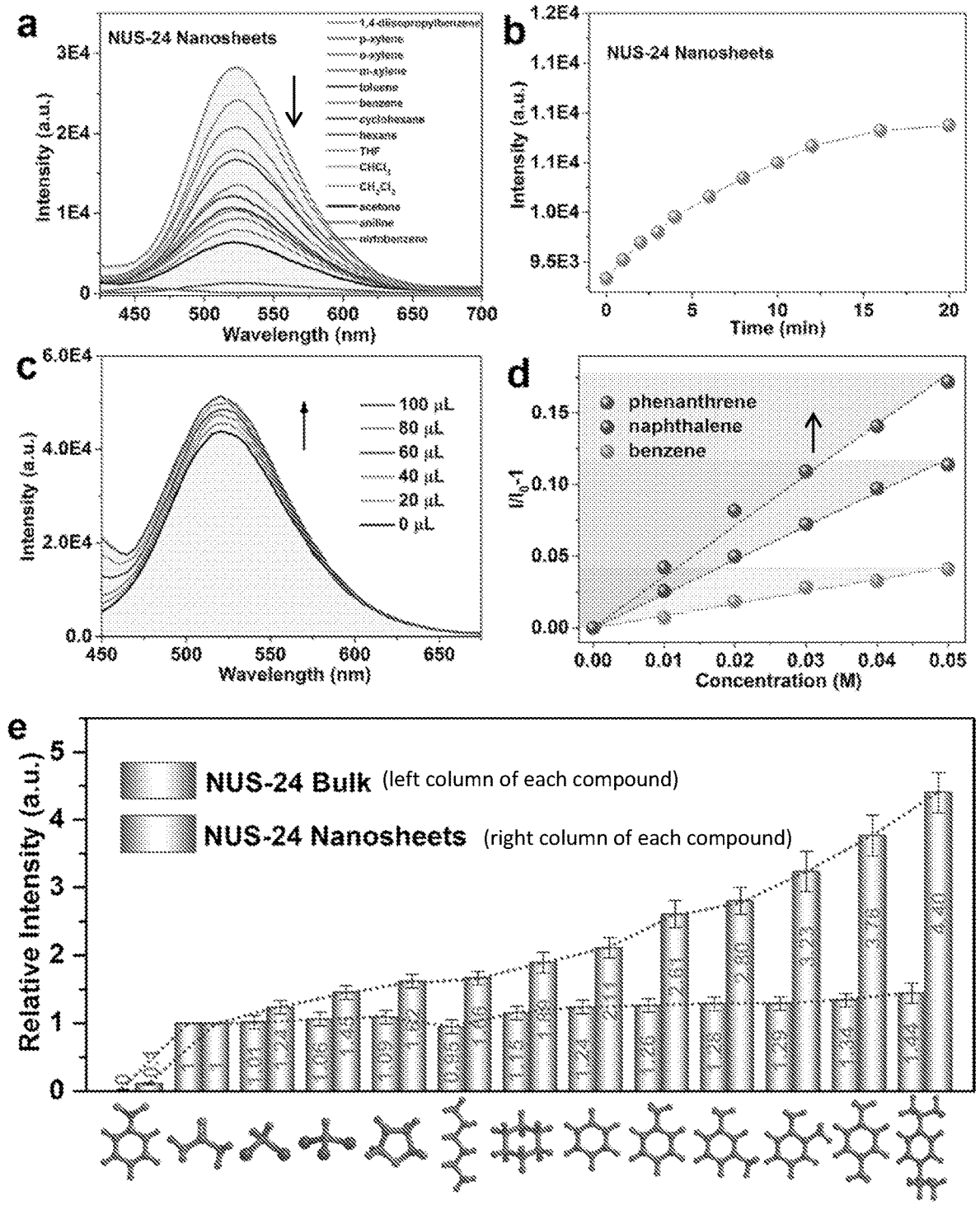

FIG. 4. NUS-24 for chemical sensing. (a) Fluorescence emission spectra of NUS-24 nanosheets in various VOC solutions at room temperature ($\lambda_{ex}$=365 nm). (b) Time-dependent fluorescence enhancement of NUS-24 nanosheets by adding 1,4-diisopropylbenzene. (c) Fluorescence emission spectra of NUS-24 nanosheets upon titration with phenanthrene. (d) Fluorescence emission intensity versus analyte concentration plots of NUS-24 nanosheets titrated with benzene, naphthalene and phenanthrene, respectively.

(e) Relative fluorescence intensity of NUS-24 bulk and NUS-24 nanosheets in various VOC solutions ($I_R=I/I_{acetone}$).

Figure 5:
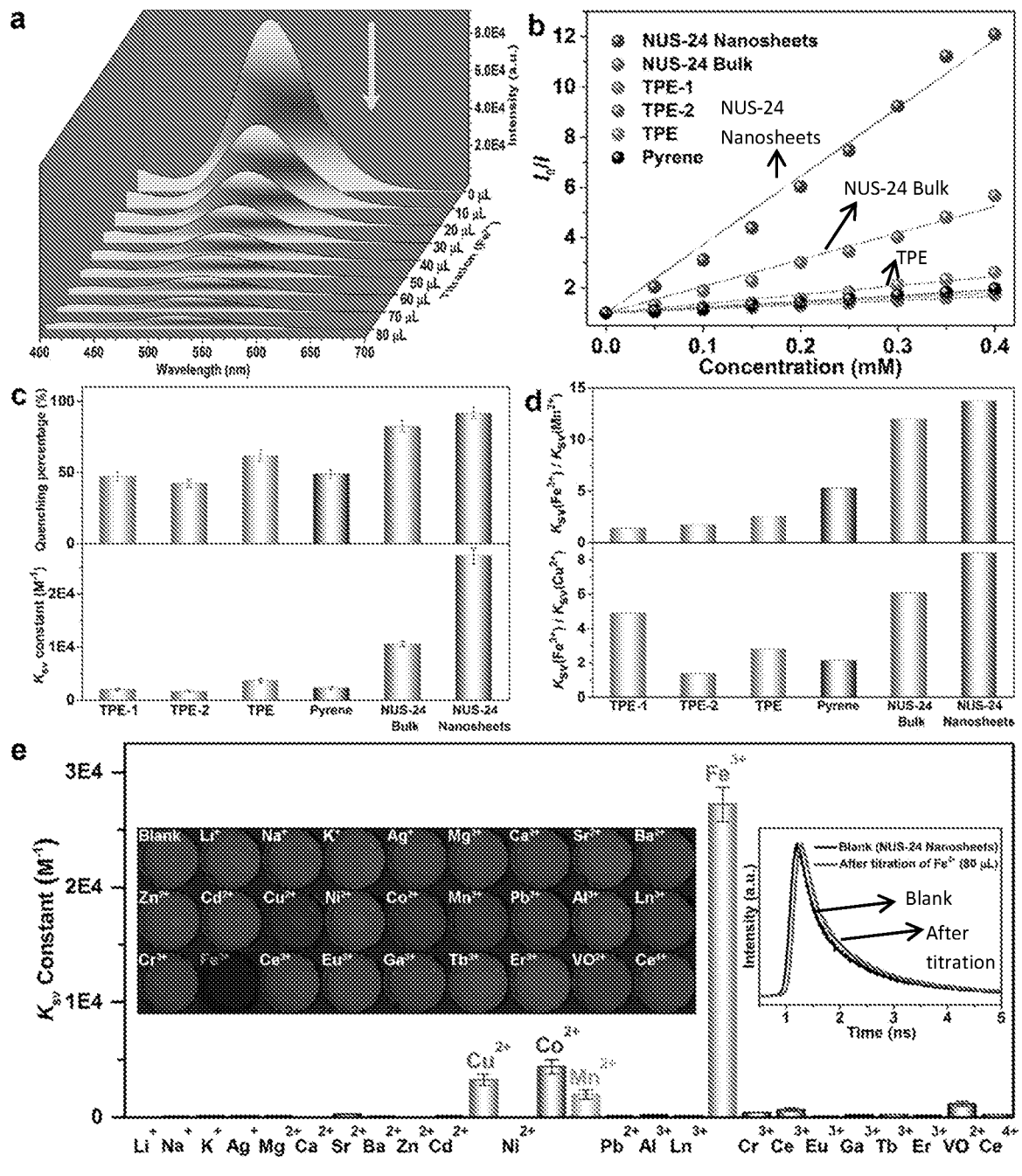

FIG. 5. Chemical sensing of metal ions by NUS-24 nanosheets. (a) Fluorescence emission spectra of NUS-24 nanosheets (c=0.1 mg mL$^{-1}$) upon titration with Fe$^{3+}$ solution (1×10$^{-2}$ M) at room temperature ($\lambda_{ex}$=365 nm). (b) Stern-Völmer plots of NUS-24 nanosheets, bulk powder and compared small molecules being titrated with Fe$^{3+}$. (c) The quenching percentages and $K_{SV}$ constants of NUS-24 nanosheets, bulk powder and compared small molecules by Fe$^{3+}$. (d) The ion selectivity of NUS-24 nanosheets, bulk powder and compared small molecules. (e) The $K_{SV}$ constants of NUS-24 nanosheets being titrated with different metal ion solutions (Left inset: fluorescent photograph of NUS-24 nanosheets upon titration with different metal ion solutions, $\lambda_{ex}$=365 nm; Right inset: emission decay trace of NUS-24 nanosheets before and after the addition of Fe$^{3+}$ solution at room temperature). The error bars in (c) and (e) show average and range of measured values based on at least five repeats in every single measurement.

Figure 6:
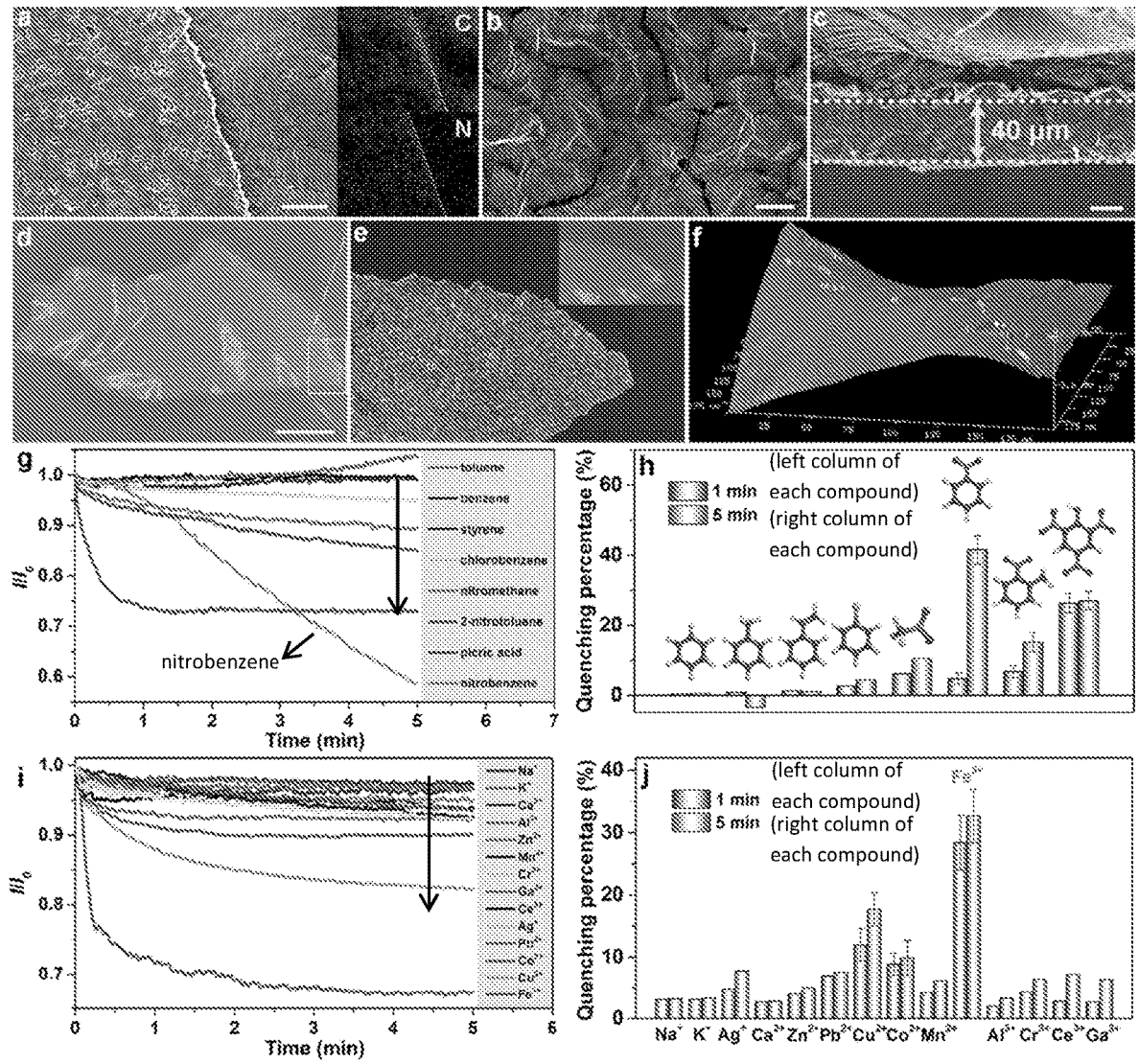

FIG. 6. Chemical sensing by MMMs containing NUS-24 nanosheets. (a,b) FE-SEM and EDX elemental mapping (carbon and nitrogen) images of the MMMs (Scale bar, 50 µm in (a) and 5 µm in (b). (c) Cross-sectional FE-SEM image of the MMMs (Scale bar, 20 µm). (d,e) Optical (d) and fluorescence (e) photographs of the MMMs ((Scale bar, 5 mm in d. $\lambda_{ex}$=365 nm). (f) AFM image of the MMMs. (g) Time-dependent fluorescence intensity changes ($I/I_0$) of the MMMs upon 5 min exposure to VOCs vapours ($\lambda_{ex}$=365 nm, $\lambda_{em}$=530 nm). (h) The quenching percentages of the MMMs by VOC vapours after 1 min and 5 min exposure. (i) Time-dependent fluorescence intensity changes ($I/I_0$) of the MMMs upon 5 min exposure to metal ion solutions ($\lambda_{ex}$=365 nm, $\lambda_{em}$=530 nm). (j) The quenching percentages of the MMMs by metal ions after 1 min and 5 min exposure. The error bars in h and j show standard deviations based on three independent measurements.

Figure 7:
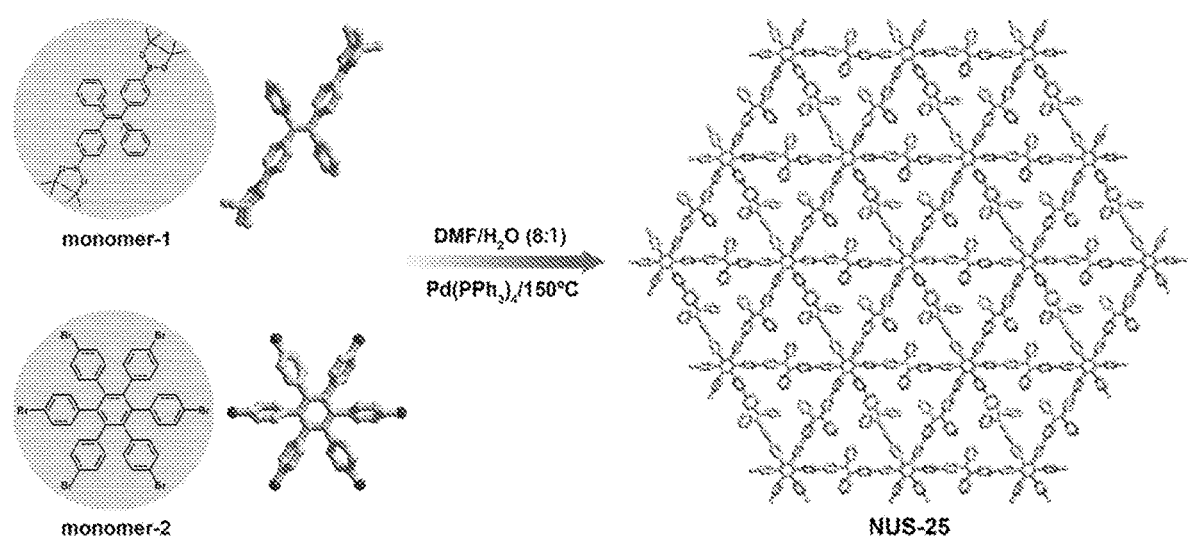

FIG. 7. Synthetic route used to form bulk NUS-25 by Suzuki-Miyaura coupling reactions.

Figure 8:
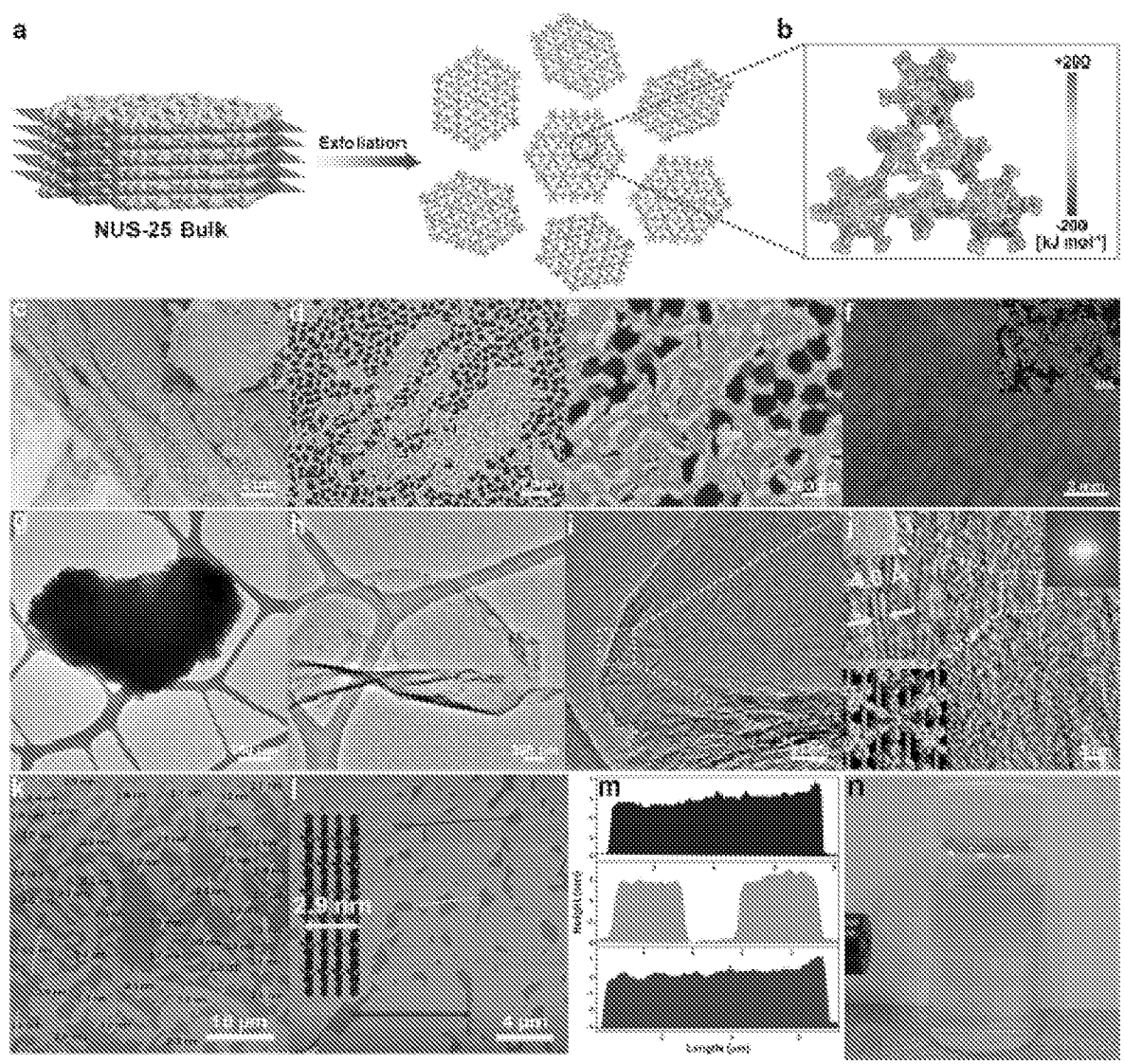

FIG. 8. FE-SEM, HR-TEM and AFM characterization of bulk and nanosheets of NUS-25. (a) The schematic diagram for the exfoliation of NUS-25 from bulk layered material to ultrathin 2D nanosheets. (b) Electrostatic potential surface of NUS-25 fragment obtained by DFT calculation. (c) FE-SEM image of NUS-25 bulk powder. The area enclosed by the dotted-rectangle indicates the layered structure. (d-e) FE-SEM images of NUS-25 nanosheets deposited on AAO substrate. (f) Fluorescence photograph of NUS-25 nanosheets ($\lambda_{ex}$=365 nm, inset: fluorescence photograph of NUS-25 bulk). (g) HR-TEM image of NUS-25 bulk powder. (h-i) HR-TEM images of NUS-25 nanosheets. (j) HR-TEM image of NUS-25 nanosheets featuring the planar lattice structure (inset: the lattice distance and the Fast Fourier transformation). The lattice structure is from (−550) plane based on the optimized AA stacking modelling structure. (k-l) AFM images of NUS-25 nanosheets exfoliated in acetonitrile solution. Inset in (l): the theoretical thickness of four layers (2.9 nm) of NUS-25 nanosheets based on the optimized AA stacking modelling structure. (m) The height of AFM image for selective area of (l). (n) The optical photograph of NUS-25 nanosheets in acetonitrile solution indicating a strong Tyndall effect.

Figure 9:
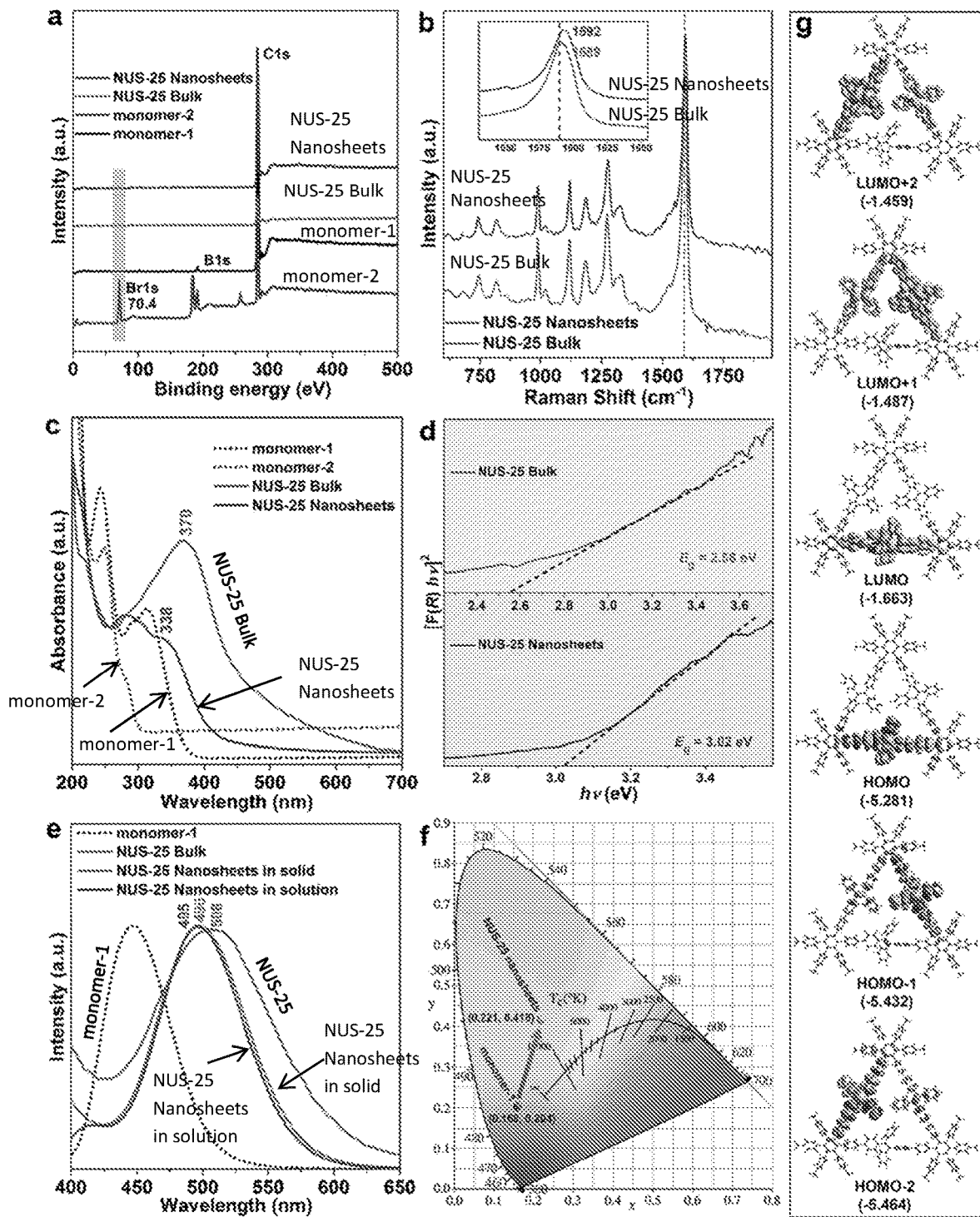

FIG. 9. Characterization of NUS-25 nanosheets. (a) Raman spectra of bulk powder and nanosheets of NUS-25. (b) XPS spectra of monomers, bulk powder and nanosheets of NUS-25. (c) UV-Vis spectra of monomers, bulk powder and nanosheets of NUS-25 in acetonitrile solution. (d) Optical band gaps (Eg) of bulk powder and nanosheets of NUS-25 in solid state by diffuse reflectance. (e) Fluorescence emission spectra of monomer-1 (solid state), bulk powder and nanosheets of NUS-25 ($\lambda_{ex}$=365 nm). (f) CIE coordinates of emission colour of monomer-1 and NUS-25 nanosheets. (g) The frontier molecular orbital distributions of NUS-25 fragment by DFT calculations.

Figure 10:
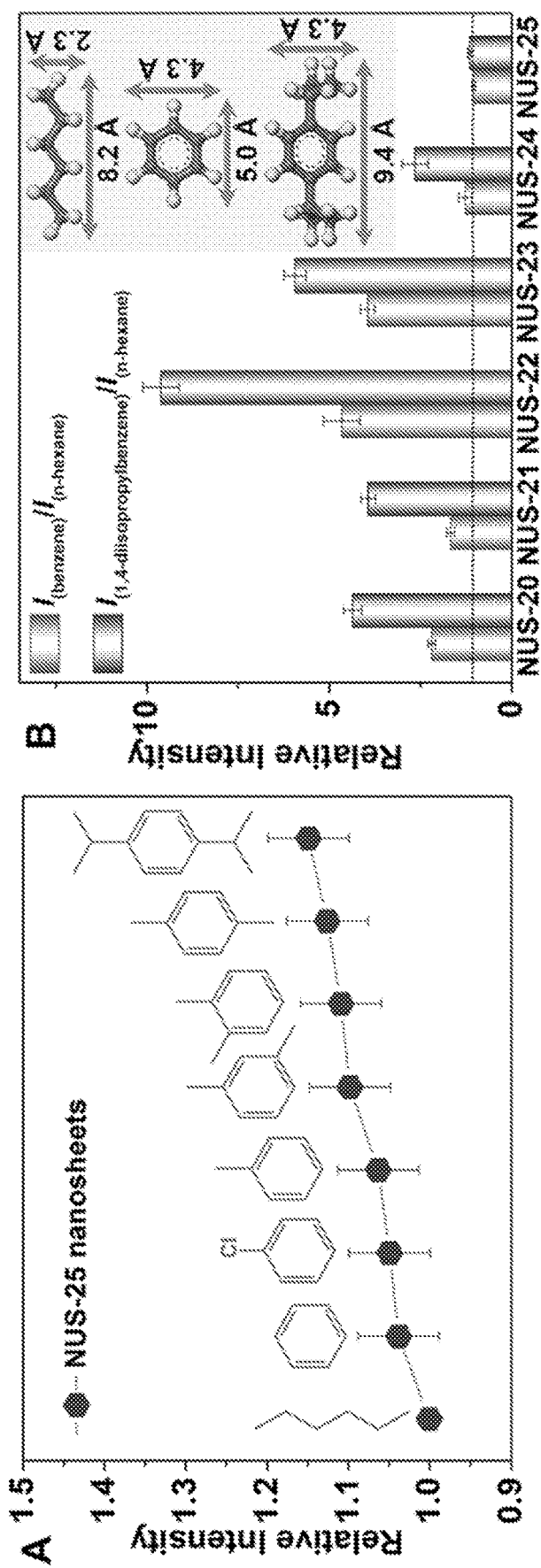

FIG. 10. (a) Relative fluorescence intensity of NUS-25 nanosheets in various VOC solutions ($I_R=I/I_{n-hexane}$). (b) Relative fluorescence intensity [$I_{(benzene)}/I_{(n-hexane)}$ and $I_{(1,4-diisopropylbenzene)}/I_{(n-hexane)}$] of NUS 20-25 in various VOCs (inset: the molecular size of n-hexane, benzene and 1,4-diisopropylbenzene).

Figure 11:
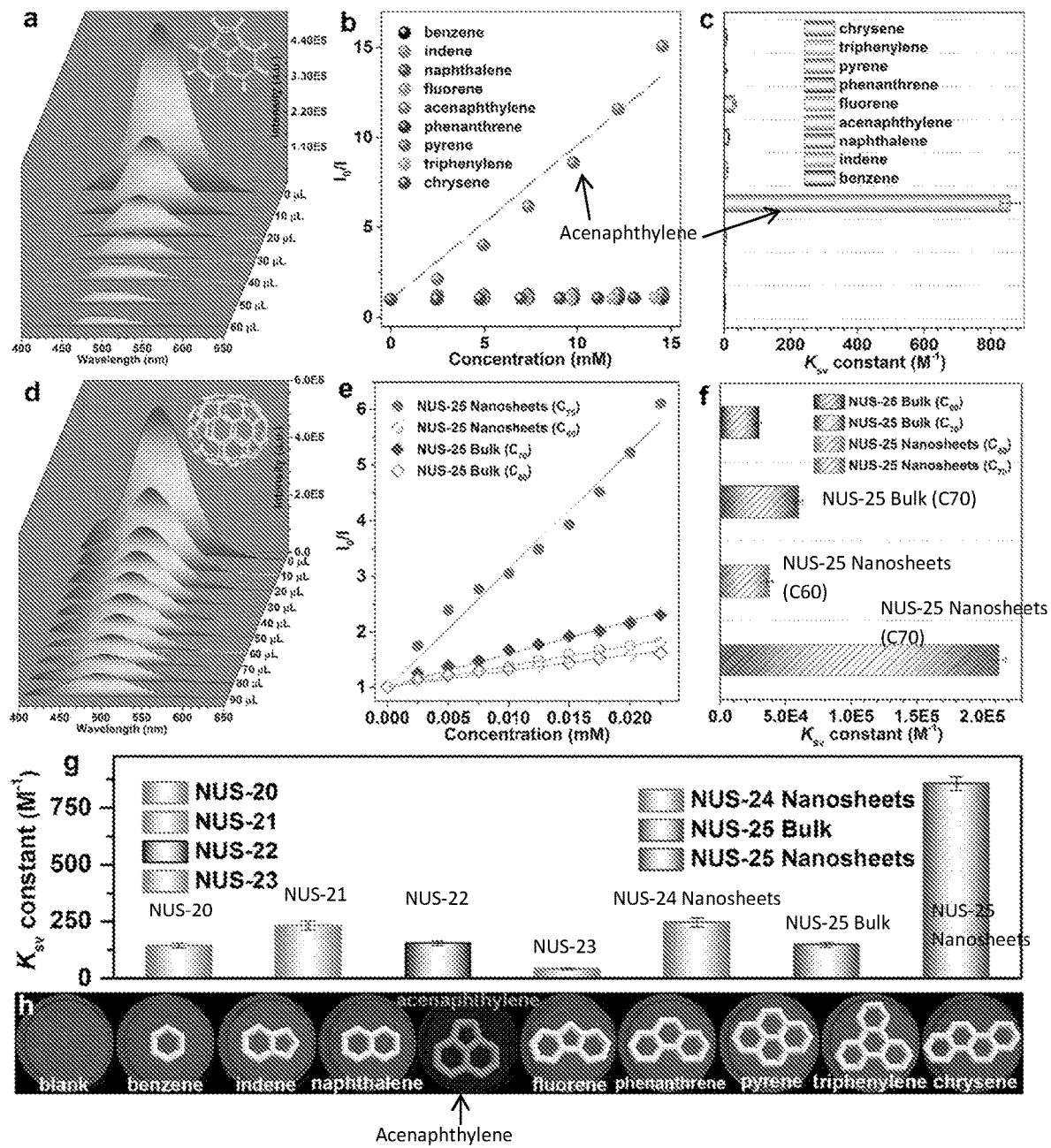

FIG. 11. Chemical sensing of PAHs by NUS-25 nanosheets. (a) Fluorescence emission spectra of NUS-25 nanosheets (c=60 µg mL$^{-1}$) upon titration with acenaphthylene solution (0.5 M in CH$_2$Cl$_2$) at room temperature ($\lambda_{ex}$=365 nm). The Stern-Völmer plots (b) and $K_{sv}$ constants (c) of NUS-25 nanosheets being titrated with PAHs. (d) Fluorescence emission spectra of NUS-25 nanosheets upon titration with C$_{70}$ solution (5×10$^{-4}$ M in toluene) at room temperature ($\lambda_{ex}$=365 nm). The Stern-Völmer plots (e) and $K_{sv}$ constants (f) of bulk and nanosheets of NUS-25 being titrated with C$_{60}$ and C$_{70}$. (g) The Stern-Völmer $K_{sv}$ constants of NUS 20-25 upon titration with acenaphthylene solution (0.5 M in CH$_2$Cl$_2$). (h) Fluorescence photographs of NUS-25 nanosheets upon titration with various PAHs ($\lambda_{ex}$=365 nm).

Figure 12:
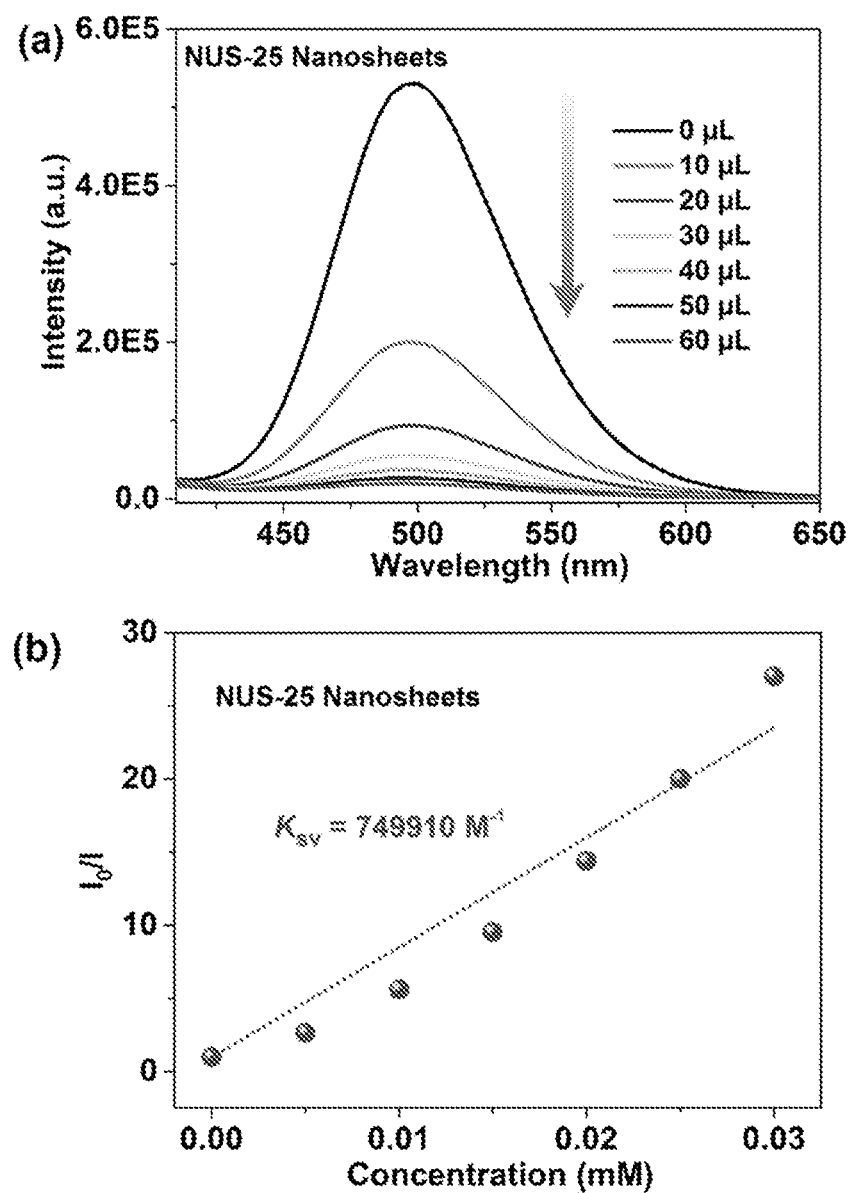

FIG. 12. Chemical sensing of nitrobenzene by NUS-25 nanosheets. (a) Fluorescence emission spectra of NUS-25 nanosheets (c=60 µg mL$^{-1}$) upon titration with nitrobenzene acetonitrile solution (1×10$^{-3}$ M) at room temperature ($\lambda_{ex}$=365 nm). (b) Stern-Völmer plots of NUS-25 nanosheets being titrated with nitrobenzene.

Figure 13:
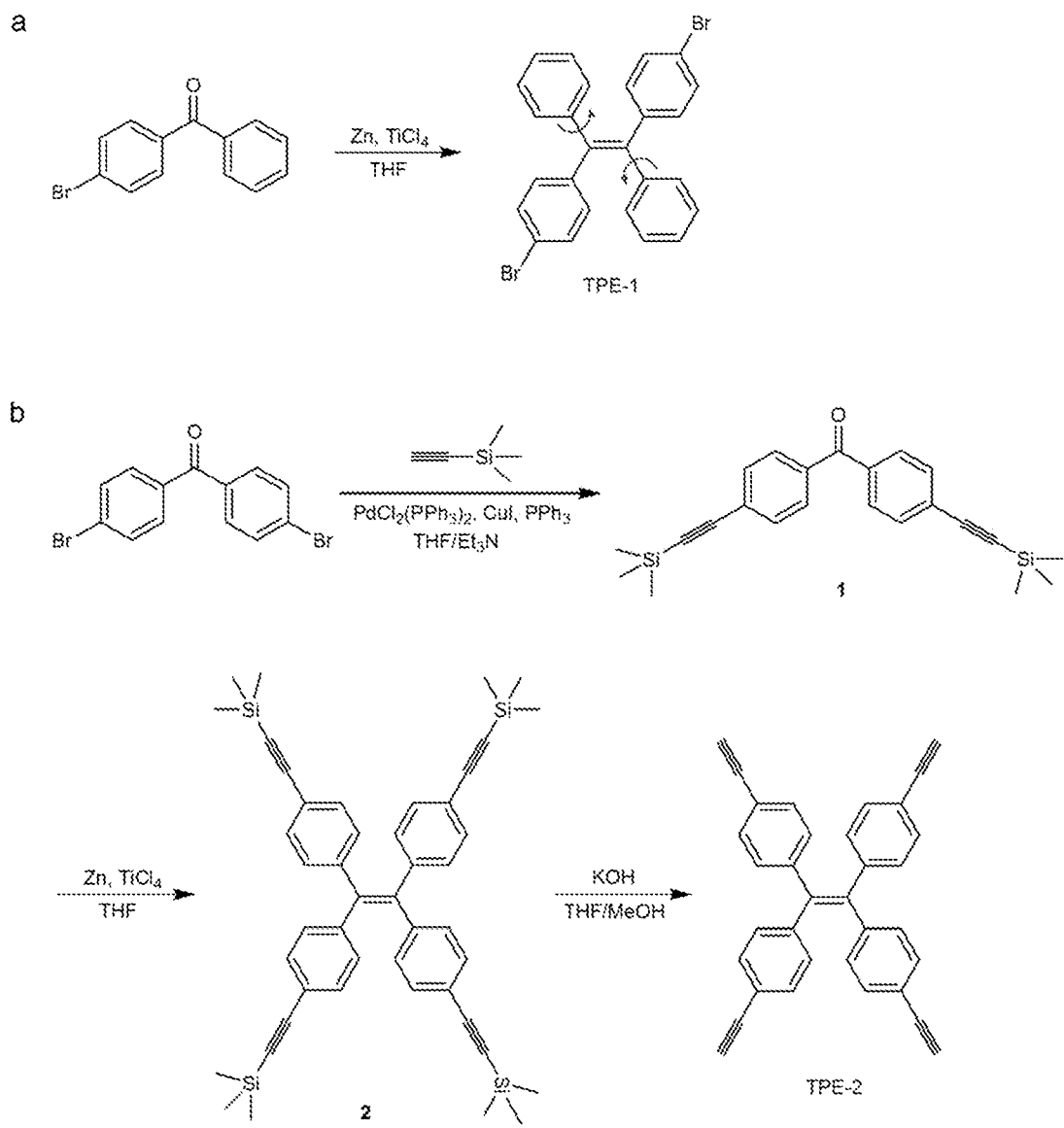

FIG. 13. Synthetic scheme for making precursors of NUS-24 (a) Synthetic scheme of TPE-1. (b) Synthetic scheme of TPE-2.

Figure 14:
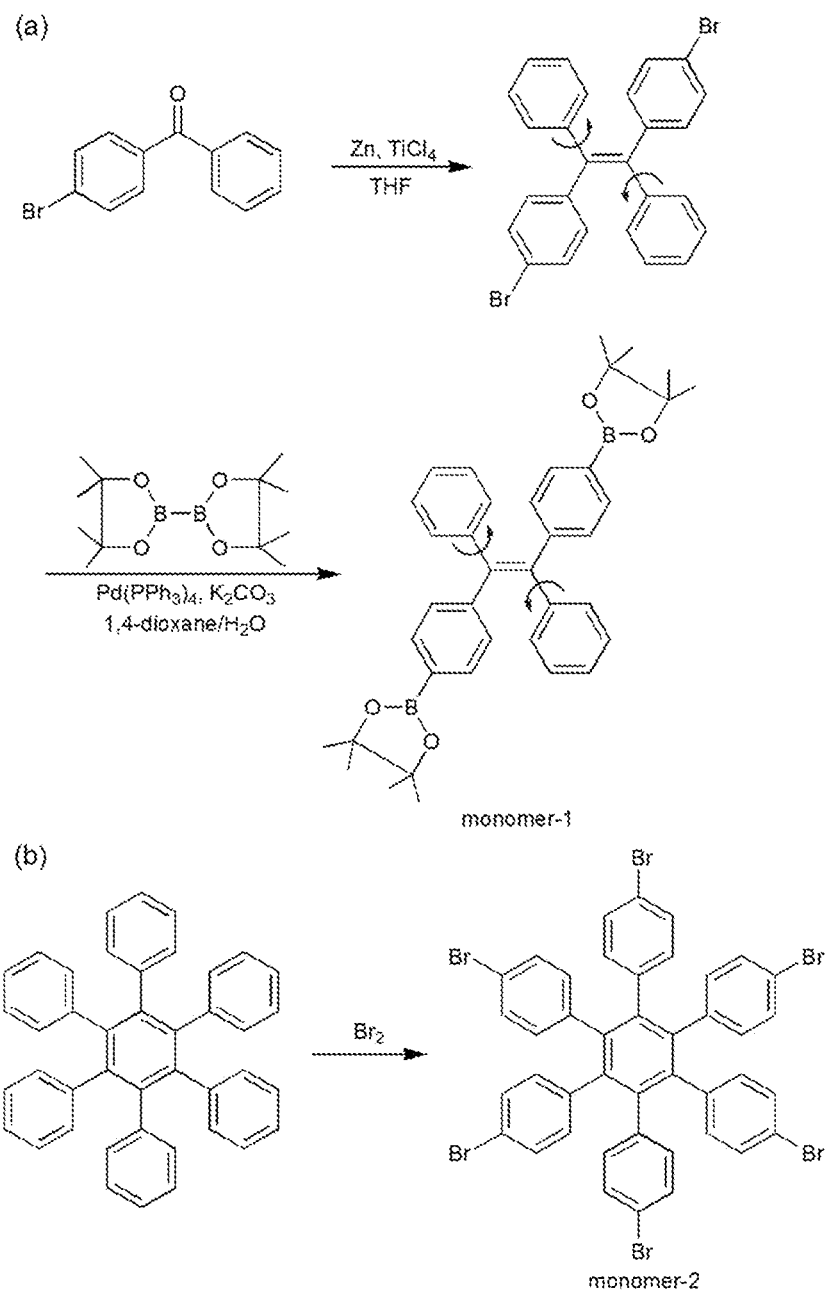

FIG. 14. Synthetic scheme for making precursors of NUS-25 (a) Synthetic scheme of monomer-1 linker. (b) Synthetic scheme of monomer-2 linker.

DESCRIPTION

This invention relates to the formation and application of two distinct π-conjugated 2D porous organic nanosheets with an all-carbon backbone, which are named herein NUS-24 and NUS-25, both of these materials contain flexible tetraphenylethylene (TPE) units as molecular rotors.

NUS-24 is a polymer having a repeating unit according to Formula (I):

wherein A represents a central portion of the polymeric repeating unit and is represented by formula (II):

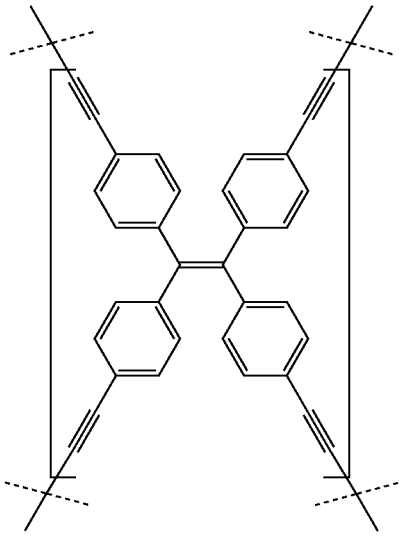

(II)

where the dotted lines relate to the points of attachment to X; and
wherein each X represents a peripheral portion of the polymeric repeating unit and is represented by formula (III):

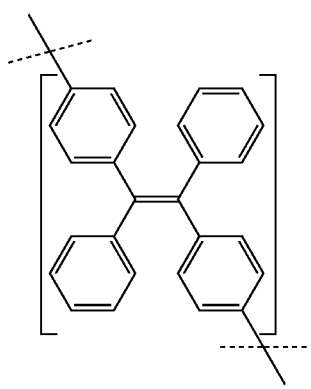

(III)

where the dotted lines relate to the points of attachment to unit A, or salts and solvates thereof. NUS-24 may be provided in a bulk form or (after exfoliation or similar processing) as nanosheets.

It will be appreciated that the polymers of formula (I) form a porous organic framework (POF). As such, reference to the polymers of formula (I) herein is also reference to the porous organic framework formed by said polymers.

Salts that may be mentioned include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of formula I in the form of a salt with another counter-ion, for example using a suitable ion exchange resin.

Examples of salts include acid addition salts derived from mineral acids and organic acids, and salts derived from metals such as sodium, magnesium, or preferably, potassium and calcium.

Examples of acid addition salts include acid addition salts formed with acetic, 2,2-dichloroacetic, adipic, alginic, aryl sulphonic acids (e.g. benzenesulphonic, naphthalene-2-sulphonic, naphthalene-1,5-disulphonic and p-toluenesulphonic), ascorbic (e.g. L-ascorbic), L-aspartic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (−)-L-malic), malonic, (±)-DL-mandelic, metaphosphoric, methanesulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, tartaric (e.g. (+)-L-tartaric), thiocyanic, undecylenic and valeric acids.

Particular examples of salts are salts derived from mineral acids such as hydrochloric, hydrobromic, phosphoric, metaphosphoric, nitric and sulphuric acids; from organic acids, such as tartaric, acetic, citric, malic, lactic, fumaric, benzoic, glycolic, gluconic, succinic, arylsulphonic acids; and from metals such as sodium, magnesium, or preferably, potassium and calcium.

As mentioned above, also encompassed by formula I are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particularly preferred solvates are hydrates, and examples of hydrates include hemihydrates, monohydrates and dihydrates.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

The polymers of formula (I) disclosed herein may provide an optical band gap of from 2.20 to 2.90 eV, meaning that they have a semiconductor nature that is capable of fluorescence emission. This in turn makes these materials suitable for use as a chemical sensor for various applications. For example, the bulk form of NUS-24 may have an optical band gap ($E_g$) of around 2.39 eV, while the nanosheets may have optical band gap of around 2.77 eV.

The polymers disclosed herein also display significant chemical and thermal stability. For example, the polymers disclosed herein can be soaked in both mineral acids (up to at least 6M) and bases (up to at least 8M), as well as common organic solvents and water without degradation, which results are discussed in more detail in the experimental section below.

Thus, the polymers disclosed herein are suitable for use in corrosive environments and/or in environments at elevated temperatures, where other chemical sensors may not be able to operate due to chemical/thermal instability under such conditions.

As discussed hereinbefore, it is important that a polymer for use in chemical sensing maintains a porous nature. The polymers disclosed herein may have a BET surface area of from 90 to 500 $m^2$ $g^{-1}$ (e.g. from 150 to 350 $m^2$ $g^{-1}$) and/or total pore volume of from 0.1 to 0.5 $cm^3$ $g^{-1}$ (e.g. from 0.13 to 0.35 $cm^3$ $g^{-1}$), which may also translate into an average pore width of from 5 to 17 Å.

When NUS-24 (i.e. the compound of formula (I)) is provided as a bulk polymer it may have one or more of the following properties:
(a) a BET surface area of from 250 to 500 $m^2$ $g^{-1}$ (e.g. 335 $m^2$ $g^{-1}$);
(b) a total pore volume of from 0.3 to 0.5 $cm^3$ $g^{-1}$ (e.g. 0.378 $cm^3$ $g^{-1}$); and
(c) micropores having a diameter of from 5 to 17 Å (e.g. 14 Å) and macropores having a diameter of from 25 to 35 Å (e.g. 28 Å).

When NUS-24 is provided as a nanosheet (or nanosheets), the nanosheet may have from one to four layers (e.g. one layer) of the polymer of formula (I). Additionally or alternatively, these nanosheets may have one or more of the following properties:
(a) a BET surface area of from 90 to 200 $m^2$ $g^{-1}$ (e.g. 92 $m^2$ $g^{-1}$ in acetonitrile, 100 $m^2$ $g^{-1}$ in acetone, or 162 $m^2$ $g^{-1}$ in ethanol);
(b) a total pore volume of from 0.1 to 0.35 $cm^3$ $g^{-1}$ (e.g. 0.13 $cm^3$ $g^{-1}$ in acetone or acetonitrile, or 0.20 $cm^3$ $g^{-1}$ in ethanol);
(c) pores having a diameter of from 5 to 17 Å (e.g. 14 Å);
(d) a sheet size of from 400 to 800 nm when measured in an organic solvent by dynamic light scattering (e.g. 404 nm when measured in acetonitrile, 529 nm when measured in acetone, or 657 nm when measured in ethanol); and
(e) a thickness of from 2 to 5 nm.

Nanosheets of NUS-24 exhibit high stability, large lateral size, and are ultrathin—having a thickness of from 2 to 5 nm. The dynamic TPE rotors exposed on the surface of NUS-24 nanosheets may be restricted in the aggregated state by different water fractions, which is reminiscent of the aggregation-induced emission mechanism, thereby leading to the size-selective turn-on fluorescence by volatile organic compounds. Significantly, the ultrathin 2D nanosheets and its composite membranes show much higher sensitivity and selectivity toward $Fe^{3+}$ ions and nitro-containing compounds sensing, suggesting their potential applications in explosive detection and environmental monitoring.

As will be appreciated, the sensing applications may be accomplished using any form of NUS-24, such as the bulk form or, more particularly, in nanosheet form or NUS-24 (in either form, but particularly the nanosheet form) within a mixed matrix membrane composite material. Said composite material may comprise a polymer of formula (I) (i.e. NUS-24) dispersed within a polymeric matrix material formed from a polymer without electron withdrawing group moieties and/or aromatic or heteroaromatic rings (i.e. a non-fluorescence polymer). For example, the polymer of the polymeric matrix may be polyethylene imine.

For certain applications discussed herein, e.g. vapour and/or solution-based sensing, it may be convenient to provide the polymers disclosed herein as a powder having a particle size of from 50 to 600 nm, whether in bulk or nanosheet form. In other applications, it may be more convenient to provide the polymer as part of a composite material, such as with a non-fluorescence polymer (e.g. poly(ethylene imine)). Additionally or alternatively, the bulk, nanosheet or composite material forms of NUS-24 may be used in combination with an optical fiber to form a sensor device.

In embodiments herein, the word "comprising" may be interpreted as requiring the features mentioned, but not limiting the presence of other features. Alternatively, the word "comprising" may also relate to the situation where only the components/features listed are intended to be present (e.g. the word "comprising" may be replaced by the phrases "consists of" or "consists essentially of"). It is explicitly contemplated that both the broader and narrower interpretations can be applied to all aspects and embodiments of the present invention. In other words, the word "comprising" and synonyms thereof may be replaced by the phrase "consisting of" or the phrase "consists essentially of" or synonyms thereof and vice versa.

NUS-24 may be prepared by any suitable method known in the art. One method that may be used to manufacture the polymers disclosed herein involves reacting a compound of formula (VI):

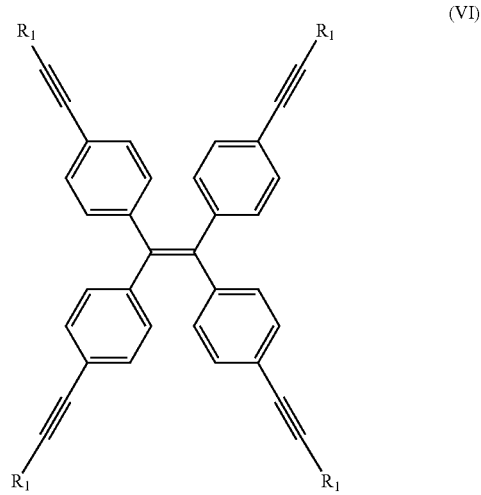

(VI)

where $R_1$ represents H, with a compound of formula (VII):

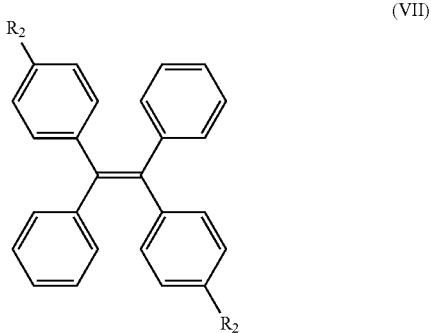

(VII)

where $R_2$ represents halo.

The term "halo", when used herein, includes references to fluoro, chloro, bromo and iodo. However, in the context of the reactions described above, it may refer to chloro, or more particularly, bromo and iodo.

The polymers of formula (I) disclosed herein have surprisingly good optical and stability properties. As such, the polymers for formula (I) may be particularly suited for use in chemical sensing and therefore there is also disclosed a chemical sensor or a biosensor or an environmental monitoring assay comprising a polymer as described hereinbefore. In certain cases, the sensor may simply be a powdered form of the polymers of formula (I) as described hereinbefore, which may be applied to a space for analysis or placed into a solution containing an analyte, or it may be provided as part of a composite material as discussed hereinbefore.

As described hereinbelow, the detection of a volatile organic compound in a liquid may be conducted by providing a portion of a polymer of formula (I) to an analyte of said liquid and then measuring the photoluminescence in a suitable testing apparatus. It has been surprisingly found that the compounds of formula (I) show a relationship between the size of the volatile organic compound(s) in the analyte and the relative fluorescence emission intensity (see Example 2 below, in particular FIGS. 4a and 4e). As such, the compounds of formula (I) may also be useful in detecting the sizes of volatile organic contaminants in a liquid, which may allow for definitive qualitative differentiation between certain compounds that are normally difficult or impossible to tell apart using conventional sensors (e.g. benzene and toluene). Given these effects, the polymers of formula (I) may allow for both qualitative identification of volatile organic compound contaminants and quantification of the amount of said contaminants in a sample analyte. These features may also apply to gaseous analysis as discussed hereinbelow.

When the polymers of formula (I) are used in sensing volatile organic compounds in vapour form, the polymers may be provided attached to a substrate that enables a photoluminescence test to be run. For example, the polymers of formula (I) may be attached to a transparent substrate that is placed or forms part of a chamber containing a gaseous analyte suitable for use in a suitable photoluminescence testing apparatus. When the polymers of formula (I) are used in this manner, it has been surprisingly found that they can be reused following a recycling step (e.g. heating at elevated temperature (such as from 70° C. to 150° C., e.g. 120° C. under vacuum) for a suitable period of time (e.g. from 10 minutes to 2 hours, such as 30 minutes).

It is noted that when the polymers of formula (I) are provided in the form of a mixed matrix membrane and exposed to a volatile organic compound, there may not be any turn-on fluorescence effect. As such, the use of the bulk or more particularly the nanosheet forms of NUS-24 may be preferred.

In addition to the above, it has also been surprisingly found that the relative fluorescence emission intensity of the polymers of formula (I) may provide a (or an almost) perfect linear relationship between turn-on fluorescence and volatile organic compound concentration from 0% to 100% of the liquid analyte (see the examples below). This may enable the polymers of formula (I) to be used quantitatively as well as qualitatively.

Suitable volatile organic compounds that may be detected include, but are not limited to, dichloromethane, chloroform, tetrahydrofuran, n-hexane, cyclohexane, benzene, naphthalene, phenathrene, toluene, o-xylene, m-xylene, p-xylene, 1,4-diisopropylbenzene, aniline, nitrobenzene and mixtures thereof. For example, the volatile organic compounds can be dichloromethane, chloroform, tetrahydrofuran, n-hexane, cyclohexane, benzene, toluene, o-xylene, m-xylene, p-xylene, 1,4-diisopropylbenzene, aniline and mixtures thereof.

In addition to the above, it has also been surprisingly found that the relative fluorescence emission intensity of the polymers of formula (I) may provide a (or an almost) perfect linear relationship between turn-on fluorescence and volatile organic compound concentration from 0 M to 0.05 M of the volatile organic compound. Volatile organic compounds that may exhibit the linear relationship include benzene, naphthalene and phenathrene. Fluorescence enhancement may be observed following the order of phenanthrene>naphthalene>benzene, consistent with the size effect elucidated previously. This may enable the polymers of formula (I) to be used quantitatively as well as qualitatively for the detection of these volatile organic compounds.

Surprisingly, a turn-off fluorescence effect occurs when the compounds of formula (I) are exposed to nitrobenzene and metal ions (e.g. $Cu^{2+}$, $Co^{2+}$, $Mn^{2+}$ and $Fe^{3+}$ (e.g. the metal ion is $Fe^{3+}$)). It is noted that a similar effect may occur when the compounds of formula (I) are exposed to other compounds having similar physiochemical properties to nitrobenzene, such as trinitrotoluene and the like.

As described hereinbelow, the detection of a metal ion in a liquid may be conducted by providing a portion of a polymer of formula (I) to an analyte of said liquid (usually the metal salt solution) and then measuring the photoluminescence in a suitable testing apparatus. It has been found that a turn-off fluorescence effect (which may also be referred herein as fluorescence quenching) occurs when the compounds of formula (I) are exposed to $Cu^{2+}$, $Co^{2+}$, $Mn^{2+}$ and $Fe^{3+}$ ions. In particular, $Fe^{3+}$ ions may exhibit a stronger turn-off fluorescence effect as compared to $Cu^{2+}$, $Co^{2+}$, $Mn^{2+}$ ions. This shows that the polymers of formula (I) may provide selective detection of $Fe^{3+}$ ions over other metal ions.

In addition to the above, it has also been surprisingly found that the fluorescence emission intensity of the polymers of formula (I) may provide a (or an almost) perfect linear relationship between turn-off fluorescence and $Fe^{3+}$ ion concentration (see FIG. 5a).

Surprisingly, a turn-off fluorescence effect occurs when the polymers of formula (I) are exposed to nitrobenzene, which is an explosive compound. It is noted that a similar effect may occur when the compounds of formula (I) are exposed to other explosive compounds, or compounds having similar physiochemical properties to nitrobenzene, such as trinitrotoluene and the like. For example, a mixed matrix membrane containing nanosheets of NUS-24 is capable of detecting nitromethane, nitrobenzene, 2-nitrotoluene and 2,4,6-trinitrophenol (picric acid) through the turn-off fluorescence effect.

The turn-off fluorescence detection of explosive compounds and/or metal ions may be run using the bulk form or nanosheets of NUS-24, but it may be particularly useful to use NUS-24 (in bulk or, more particularly, nanosheet form) in a mixed-matrix membrane as the turn-off fluorescence effect is not affected by incorporations into a polymer matrix.

NUS-25 is a polymer having a repeating unit according to Formula (IV):

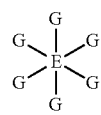

(IV)

wherein E represents a central portion of the polymeric repeating unit and is represented by

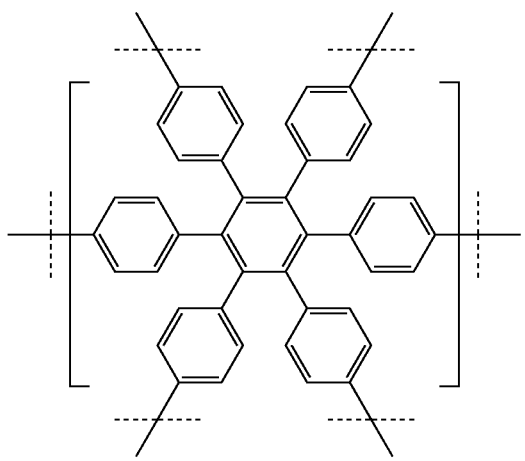

(V)

formula (V):
where the dotted lines relate to the points of attachment to G; and wherein each G represents a peripheral portion of the polymeric repeating unit and is represented by formula (III):

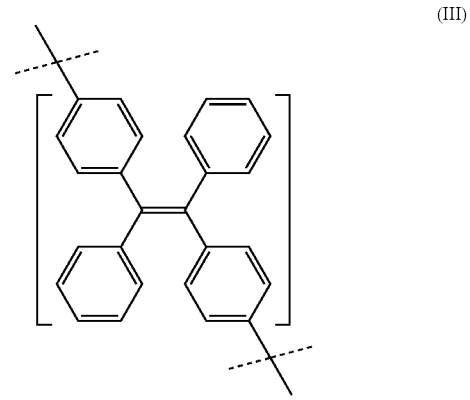

(III)

where the dotted lines relate to the points of attachment to unit A, or salts and solvates thereof. NUS-25 may be provided in a bulk form or (after exfoliation or similar processing) as nanosheets. The salts and solvates mentioned above for the polymer of formula (IV) may be as defined hereinbefore.

It will be appreciated that the polymers of formula (IV) also form a porous organic framework (POF). As such, reference to the polymers of formula (IV) herein is also reference to the porous organic framework formed by said polymers.

The polymers of formula (IV) disclosed herein may provide an optical band gap of from 2.50 to 3.10 eV, meaning that they have a semiconductor nature that is capable of fluorescence emission. This in turn makes these materials suitable for use as a chemical sensor for various applications. The polymers of formula (IV) disclosed herein may have a fluorescence emission peak at from around 496 nm to around 508 nm.

As discussed hereinbefore, it is important that a polymer for use in chemical sensing maintains a porous nature. The polymers disclosed herein may have a BET surface area of from 150 to 750 m² g⁻¹ (e.g. from 180 to 650 m² g⁻¹) and/or total pore volume of from 0.1 to 0.9 cm³ g⁻¹ (e.g. around 0.69 cm³ g⁻¹), which may also translate into an average pore width of from 5 to 17 Å.

For certain applications discussed herein, e.g. vapour and/or solution-based sensing, it may be convenient to provide the polymers disclosed herein as a powder having a particle size of from 50 to 600 nm (whether in bulk or in nanosheet form).

When NUS-25 (i.e. the compound of formula (I)) is provided as a bulk polymer it may have one or more of the following properties:
(a) a BET surface area of from 450 to 750 m² g⁻¹ (e.g. 623 m² g⁻¹);
(b) a total pore volume of from 0.5 to 0.9 cm³ g⁻¹ (e.g. 0.69 cm³ g⁻¹); and
(c) pores having a diameter of from 5 to 17 Å (e.g. 12.6 Å).

When NUS-25 is provided as a nanosheet (or nanosheets), the nanosheet may have from one to four layers (e.g. one layer) of the polymer of formula (I). Additionally or alternatively, these nanosheets may have one or more of the following properties:

(a) a BET surface area of from 150 to 300 m² g⁻¹ (e.g. 184 m² g⁻¹ as measured in acetonitrile);

(b) a sheet size of from 2 to 20 μm (e.g. 4 μm) when measured in an organic solvent by dynamic light scattering; and (c) a thickness of from 2 to 5 nm (e.g. 3 nm).

NUS-25 bulk powder can be easily exfoliated into micrometre-sized lamellar freestanding nanosheets having a thickness of 2-5 nm. The dynamic behaviour of the TPE rotors is partially restricted through noncovalent interactions in the ultrathin 2D nanosheets. Because of the partially restricted TPE rotors, NUS-25 nanosheets are highly fluorescent, allowing NUS-25 nanosheets to be used as a chemical sensor for the specific detection of acenaphthylene among a series of polycyclic aromatic hydrocarbons (PAHs) via fluorescent quenching mechanism. It is shown that NUS-25 nanosheets have much higher sensitivity and selectivity than its stacked bulk powder and other similar polymers containing dynamic TPE rotors. The highly efficient molecular recognition can be attributed to the photoinduced electron transfer (PET) from NUS-25 nanosheets to acenaphthylene.

NUS-25 may be prepared by any suitable method known in the art. One method that may be used to manufacture the polymers disclosed herein involves reacting a compound of formula (VIII):

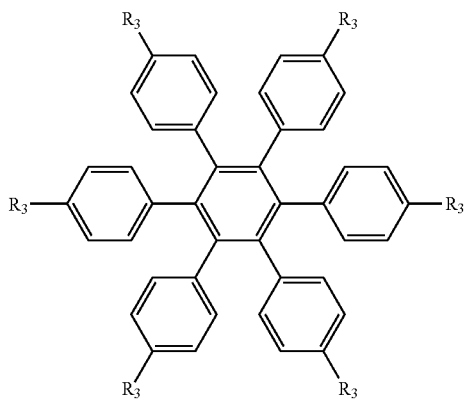

(VIII)

where $R_3$ represents halo, with a compound of formula (IX):

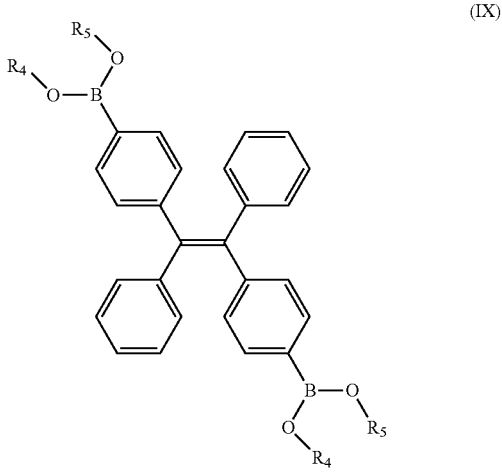

(IX)

wherein $R_4$ and $R_5$ independently represent $C_{1-6}$ alkyl, or $R_4$ and $R_5$ together with the boron and oxygen atoms to which they are attached form a 5- to 6-membered ring (e.g. a 5-membered ring), which latter two groups are unsubstituted or are substituted with from one to four substituents (e.g. four) selected from $C_{1-6}$ alkyl (e.g. methyl). As noted, the resulting bulk form of NUS-25 may be subsequently exfoliated by any suitable method to provide nanosheets of NUS-25.

Unless otherwise stated, the term "alkyl" refers to an unbranched or branched, cyclic, saturated unsubstituted group. Where the term "alkyl" is a cyclic group (which may be where the group "cycloalkyl" is specified), it is preferably $C_{3-4}$ cycloalkyl. Halo is as hereinbefore defined.

As described herein, the detection of a volatile organic compound in a liquid may be conducted by providing a portion of a polymer of formula (IV) to an analyte of said liquid and then measuring the photoluminescence in a suitable testing apparatus. It has been found that a turn-on fluorescence effect may occur in the presence of volatile organic compound(s) (e.g. see FIG. 10a). Given this, the polymers of formula (IV) may allow for qualitative identification of volatile organic compound contaminants.

Surprisingly, a turn-off fluorescence effect occurs when the polymers of formula (IV) are exposed to nitrobenzene (FIG. 12a), which is an explosive compound. It is noted that a similar effect may occur when the compounds of formula (IV) are exposed to other explosive compounds, or compounds having similar physiochemical properties to nitrobenzene, such as trinitrotoluene and the like (e.g. nitromethane, 2-nitrotoluene and 2,4,6-trinitrophenol). In addition to the above, it has also been surprisingly found that the fluorescence emission intensity of the polymers of formula (IV) may provide a (or an almost) perfect linear relationship between turn-off fluorescence and nitrobenzene concentration (see FIG. 12b).

Also surprisingly, the turn-off fluorescence effect also occurs when the polymers of formula (IV) (i.e. NUS-25) are exposed to polycyclic aromatic hydrocarbons (PAHs). Suitable PAHs that may be detected include but are not limited to fullerene, acenapthylene, pyrene, phenanthrene, fluorene, and triphenylene.

It has been surprisingly found that the fluorescence quenching of the polymers of formula (IV) may provide a (or an almost) perfect linear relationship between turn-off fluorescence and acenapthylene concentration. It has also been surprisingly found the fluorescence quenching of polymers of formula (IV) by acenaphthylene may be easily identified from fluorescence microscopy images, which may allow for the naked-eye detection of toxic PAHs, especially acenaphthylene.

The fluorescence quenching of the polymers of formula (IV) may also provide a (or an almost) perfect linear relationship between turn-off fluorescence and $C_{70}$ or $C_{60}$ concentration, which as discussed below may allow for the definitive qualitative differentiation between $C_{70}$ and $C_{60}$ using a simple test.

The invention will now be further described with reference to the following non-limiting examples.

EXAMPLES

Materials and Methods

All the reagents were obtained from commercial suppliers and used without further purification. Nuclear magnetic resonance spectroscopy (NMR) data were collected on a Bruker Avance 400 MHz NMR spectrometer (DRX400). FTIR spectra were obtained with a Bio-Rad FTS-3500 ARX FTIR spectrometer. UV-Vis spectra were collected in the solid state on a Shimadzu UV-3600 spectrometer using the $BaSO_4$ reflectance standard at room temperature. XPS experiments were performed with a Kratos AXIS Ultra DLD surface analysis instrument using a monochromatic Al Kα radiation (1486.71 eV) at 15 kV as the excitation source. PXRD patterns were obtained on a Rigaku MiniFlex 600 X-ray powder diffractometer equipped with a Cu sealed tube (λ=1.54178 Å) at a scan rate of 2° per min. TGA were performed using a Shimadzu DTG-60AH in the temperature range of 100-750° C. under flowing air (50 mL min-1) and a heating rate of 10° C. per min. DSC analyses were carried out with a Mettler Toledo DSC822e DSC under $N_2$ atmosphere with a cooling/heating rate of 20° C. per min. FE-SEM was conducted on a JEOL JSM-7610F scanning electron microscope. Samples were treated via Pt sputtering for 90 s before observation. TEM was conducted on a JEOL JEM-3010 transmission electron microscope. AFM was conducted by testing samples deposited on silica wafers using tapping mode with a Bruker Dimension Icon atomic force microscopes. $N_2$ sorption isotherms were measured using a Micromeritics ASAP 2020 surface area and pore size analyzer. Before the measurements, the samples were degassed under high vacuum (<0.01 Pa) at 120° C. for 10 h. UHP grade helium and nitrogen were used for all the measurements. Fluorescence spectra were collected at room temperature on a Photon Technology International/Quanta-Master (PTI/QM, USA) spectrometer. Fluorescent microscopy images were acquired at an excitation wavelength of 365 nm using a Nikon Ti-U fluorescence microscope equipped with a 430 nm LP filter.

Preparation of TPEs and Monomers

Synthesis of 1,2-bis(4-bromophenyl)-1,2-diphenylethene (TPE-1—see FIG. 13a). TPE-1 linker was synthesized following the procedure reported (Hu, R. et al. *J. Mater. Chem.* 22, 232-240 (2012)). A mixture of 4-bromobenzophenone (2.61 g, 10 mmol) and zinc dust (1.95 g, 30 mmol) was placed in a 250 mL two-necked round-bottom flask. The flask was evacuated under vacuum and flushed with dry nitrogen three times. After tetrahydrofuran (THF) (80 mL) was added, the mixture was cooled down to 0° C., then 1.65 mL (15 mmol) of $TiCl_4$ was added dropwise using a syringe. After refluxed for 12 h, the mixture was quenched with 10% aqueous $K_2CO_3$ solution and filtered, the filtrate was extracted with dichloromethane (DCM) three times. Solvent was removed under reduced pressure and the residue was purified by column chromatography using n-hexane as eluent. A white powder of TPE-1 linker was obtained with a yield of 65% (1.59 g). 1H NMR (400 MHz, $CDCl_3$): b (ppm) 7.27-7.21 (m, 4H), 7.15-7.13 (m, 3H), 7.11-7.10 (m, 3H), 7.01-6.98 (m, 4H), 6.91-6.87 (m, 4H).

Synthesis of 1,1,2,2-tetrakis(4-ethynylphenyl)ethane (TPE-2—see FIG. 13b). TPE-2 linker was synthesized following the procedure reported (Wang, J. et al. *Macromolecules* 45, 7692-7703 (2012)). TPE-2 linker was synthesized in a three-step process. First, a mixture of 4,4'-dibromobenzophenone (1.70 g, 5 mmol), $PdCl_2(PPh_3)_2$ (140.38 mg, 0.2 mmol), CuI (76.18 mg, 0.4 mmol) and $PPh_3$ (157.37 mg, 0.6 mmol) was placed in a 250 mL two-necked round-bottom flask. The flask was evacuated under vacuum and flushed with dry nitrogen three times. A mixture of THF (20 mL) and triethylamine (TEA) (20 mL) was then added and stirred for 1 h, then trimethylsilylacetylene (1.77 mL, 12.5 mmol) was added dropwise by a syringe. The mixture was stirred for 24 h at 50° C. Afterwards, the precipitate was removed by filtration, and the filtrate was under reduced pressure to remove solvent and the residue was purified by column chromatography using n-hexane as eluent. A white powder of 4,4'-bis(trimethylsilyl)benzophenone (1) was obtained with the yield of 78% (1.46 g). Second, a mixture of compound 1 (1.12 g, 3 mmol) and zinc dust (0.59 g, 9 mmol) was placed in a 250 mL two-necked round-bottom flask. The flask was evacuated under vacuum and flushed with dry nitrogen three times. After THF (40 mL) was added, the mixture was cooled down to 0° C. Then 0.50 mL (4.5 mmol) of $TiCl_4$ was added dropwise using a syringe. After refluxed for 12 h, the mixture was quenched with 10% aqueous $K_2CO_3$ solution and filtered, the filtrate was extracted with DCM three times, then solvent was removed under reduced pressure and the residue was purified by column chromatography using n-hexane as eluent. A pale yellow powder of 1,1,2,2-tetrakis(4-(trimethylsilylethynyl)phenyl)ethene (2) was obtained in the yield of 71% (0.76 g). Lastly, compound 2 (0.72 g, 1 mmol), KOH (1.12 g, 20 mmol), and a mixture of THF (20 mL) and methanol (20 mL) was added in a 250 mL round-bottom flask. The mixture was stirred for 12 h at room temperature. After removing solvent under reduced pressure, 1 M HCl solution (20 mL) was added and then extracted by DCM three times. Afterwards, the solvent was removed and the residue was purified by column chromatography using n-hexane as eluent. A yellow powder of TPE-2 linker was obtained in the yield of 82% (0.35 g). 1H NMR (400 MHz, CDCl3): δ (ppm) 7.26-7.24 (d, 8H), 6.95-6.92 (d, 8H), 3.06 (s, 4H).

Monomer-1 and monomer-2 were synthesized according to the published procedures (see FIG. 14): (1) Dong, J.; Tummanapelli, A. K.; Li, X.; Ying, S.; Hirao, H.; Zhao, D. *Chem. Mater.* 2016, 28, 7889-7897; (2) Lei, S.; Ver Heyen, A.; De Feyter, S.; Surin, M.; Lazzaroni, R.; Rosenfeldt, S.; Ballauff, M.; Lindner, P.; Mossinger, D.; Hoger, S. *Chem.— Eur. J.* 2009, 15, 2518-2535; (3) Hu, R.; Maldonado, J. L.; Rodriguez, M.; Deng, C.; Jim, C. K.; Lam, J. W.; Yuen, M. M.; Ramos-Ortiz, G.; Tang, B. Z. *J. Mater. Chem.* 2012, 22, 232-240.

EXAMPLES

Example 1: Synthesis and Characterization of NUS-24

Synthesis of NUS-24 Bulk Powder

NUS-24 bulk powder was synthesized using Sonogashira-Hagihara coupling reactions. Briefly, a mixture of 1,2-bis (4-bromophenyl)-1,2-diphenylethene (TPE-1, 196 mg, 0.4 mmol), 1,1,2,2-tetrakis(4-ethynylphenyl)ethane (TPE-2, 86 mg, 0.2 mmol), tetrakis(triphenylphosphine) palladium (11.6 mg, 0.01 mmol), and copper(I) iodide (38 mg, 0.2 mmol) in N,N-dimethylformamide/triethylamine (8 mL/8 mL) was degassed and purged with nitrogen. The mixture was stirred at 90° C. for 72 h and then cooled to room temperature before being poured into water. The precipitate was collected by filtration, repeatedly rinsed with hydrochloric acid (2 M), water, tetrahydrofuran, ethanol, dichloromethane, acetone, and then rigorously washed by Soxhlet extraction for 24 h with each of chloroform, tetrahydrofuran, and acetone sequentially, and finally dried in vacuum to give NUS-24 bulk powder (187.5 mg, 84% yield) as a deep yellow powder.

Preparation of NUS-24 Nanosheets

NUS-24 nanosheets were prepared from NUS-24 bulk powder by ultrasonic exfoliation in organic solvents. Briefly, 10 mg of the NUS-24 bulk powder sample was suspended in 10 mL of solvent (acetone, acetonitrile, or ethanol), and was sonicated with a frequency of 40 kHz for 6 h to give a homogeneous dispersion. The resulting dispersion was centrifuged at 3500 rpm for 5 min. The supernatant was collected was subjected to further centrifugation at 8000 rpm for 10 min to further remove non-exfoliated powder.

Characterization of NUS-24 Bulk Powder and Nanosheets

As seen in FIG. 1, 1,2-bis(4-bromophenyl)-1,2-diphenylethene (TPE-1) and 1,1,2,2-tetrakis(4-ethynylphenyl)ethane (TPE-2) were employed to synthesize NUS-24.

Computational Rotational Energy Barrier Analysis

To examine the role of free phenyl groups of TPE-1, 37 cluster models were constructed containing one TPE-1 linker and two TPE-2 linkers to evaluate the rotational energy barrier. The dangling bonds in the cluster models were saturated by H atoms. The rotor angle around the C—C bonds between two free phenyl groups varied from 0° to 360° with an interval of 10°. The constraint optimization was carried out using the B3LYP functional with 6-31G(d) basis set, followed by the simple point energy calculation at M062X/6-31+G(d) level in a solvent (acetone) (Zhao, Y. & Truhlar, D. G. *Theor. Chem. ACC.* 120, 215-241 (2008)). The solvent was represented by a polarizable continuum model (Foresman, J. B. et al. *J. Phys. Chem.* 100, 16098-16104 (1996)) and the thermal correction to Gibbs free energy was estimated at 298 K. All the DFT calculations were performed by Gaussian 09.

FIG. 1c illustrates the potential energy as a function of rotor angle. Several minima are observed at 50°, 130°, 240° and 320°, implying the existence of stable conformations. While at 90°, 180° and 290°, maxima are seen with relatively higher energy for less favorable conformations. Three rotation barriers exist with the highest barrier of 14.0 kcal mol$^{-1}$ at 180°; and the other two barriers are 5.1 and 8.0 kcal mol$^{-1}$ at 50° and 290°, respectively. Thus, it is believed that the TPE-1 linker contains dynamic molecular rotors suitable for the construction of highly efficient 2D nanomaterials with potential applications in molecular recognition and sensing.

As illustrated in FIG. 1a, layered bulk NUS-24 was successfully synthesized through Sonogashira-Hagihara coupling reaction with a yield of 84%, leading to an inherently layered porous framework with built-in TPE rotors. Compared to the polycondensation reactions used in generating 2D covalent organic frameworks (COFs) with strong interlayer interactions, the C—C coupling reaction used in NUS-24 forms strong covalent bonds within each layer, but only affords weak interlayer interactions. This is due to the irreversibility of the C—C coupling reaction and the presence of twisted TPE rotors that may prevent effective interlayer packing. The resultant structure is a highly distorted aromatic framework that favors its exfoliation and dispersion into few-layered 2D nanosheets. Thereby, the freestanding ultrathin NUS-24 nanosheets can be readily obtained by liquid exfoliation of its bulk powder (FIG. 1b). In this process, solvent molecules can enter the interlamination spaces and expand them, and finally cleave the 2D layered bulk material into few-layered nanosheets. A wide range of solvents with different surface tensions were tested, and it was found that acetone, acetonitrile and ethanol were good at exfoliating NUS-24 bulk powder. As a result, the TPE rotors, which were originally restricted by the interlayer interactions between the adjacent packing layers in the bulk powder, become fully liberated and exposed on the surface of NUS-24 ultrathin nanosheets, which is believed to contribute to the enhanced sensitivity in chemical sensing applications displayed by this material (see below).

Spectral Analysis

Fourier transform infrared spectroscopy (FT-IR) spectra show almost complete disappearance of C—Br vibration bands (around 590 cm$^{-1}$) in both NUS-24 bulk powder and NUS-24 nanosheets, indicating the completion of the cross-coupling reaction. X-ray photoelectron spectroscopy (XPS) spectra further confirms the vanishing of the Brls peak (at around 70.7 eV) in both bulk powder and nanosheets of NUS-24 (FIG. 2a). In addition, no obvious shift of the Cis binding energy is observed between bulk powder and nanosheets, suggesting identical chemical structures between these two forms of NUS-24. The chemical structure of bulk NUS-24 was further characterized by solid-state $^{13}$C CP/MAS NMR spectroscopy, which displays one main peak at 63.50 ppm assignable to the TPE-2 linker.

Raman spectra of the bulk powder and as-exfoliated nanosheets of NUS-24 show nearly identical main peaks located at around 1585 cm$^{-1}$ (FIG. 2b), which can be assigned to the carbon vibration of sp$^2$ hybridization. This further confirms the structural similarity between bulk powder and exfoliated nanosheets. However, compared to NUS-24 bulk, the Raman spectrum of NUS-24 nanosheets shows a slight shift toward high wavenumber, which can be attributed to the ultrathin thickness of the 2D nanosheets. Meanwhile, the UV-Vis spectrum of the NUS-24 nanosheets has a blue shift of about 65 nm compared to that of the bulk powder (430 nm vs. 365 nm), which is mainly due to the reduced interlayer π-π interaction in the nanosheets compared to the bulk material (FIG. 2c). Such a change in the level of π-π interaction results in a sharp increase in the optical band gap ($E_g$), from 2.39 eV in bulk powder to 2.77 eV in nanosheets (FIG. 2d). In addition, the fluorescence emission of nanosheets was also blue-shifted by about 15 nm compared to that of bulk powder (535 nm vs. 520 nm, FIG. 2e). The observed emission colours of TPE-1, TPE-2, NUS-24 bulk and NUS-24 nanosheets are differentiable on the Commission Internationale de L'Eclairage (CIE) chromaticity diagram (FIG. 2f).

No diffraction peak can be observed in the powder X-ray diffraction (PXRD) pattern of both NUS-24 bulk powder and its 2D nanosheets, indicating its amorphous nature similar to other polymers obtained via C—C cross-coupling reactions.

Electronic Structure Calculations

To quantitatively evaluate the interactions between NUS-24 and VOC molecules, the electronic properties of a NUS-24 fragment and eight VOC molecules, i.e., n-hexane, 1,4-diisopropylbenzene, p-xylene, toluene, benzene, 2-nitrotoluene, nitrobenzene and 2,4,6-trinitrophenol, were calculated using DFT. Initially, the simulated structure of NUS-24 was optimized by Forcite using Materials Studio to remove geometric distortions. Then, an NUS-24 fragment with a complete ring containing all typical building blocks was used in DFT calculations. The cleaved bonds of the ring were terminated by hydrogen atoms. The VOC molecules were optimized using the B3PW912 hybrid functional with 6-31G(d) basis set. The HOMO and LUMO energy levels of the NUS-24 fragment and VOC molecules were calculated using the B3PW91 hybrid function with 6-311G** basis set. The B3PW91 function was developed by Becke (Becke, A. D. *J. chem. Phys* 98, 5648-5652 (1993)) and demonstrated to be computationally accurate and fast for band gap calculations (Crowley, J. M., Tahir-Kheli, J. & Goddard III, W. A. *J. Phys. Chem. Lett.* 7, 1198-1203 (2016)). All the DFT calculations were carried out using Gaussian 09.

DFT calculations were performed to examine the electronic structures of NUS-24 (FIG. 2g). The calculated frontier orbitals of NUS-24 fragment indicate that the characteristics of their individual components are maintained due to the absence of electron-withdrawing group, which is helpful for fluorescence emission. For the nanosheets, the main UV-Vis absorption band centers at around 365 nm, corresponding to the HOMO to LUMO transition based on the DFT calculation. Moreover, the high electrostatic surface potential of NUS-24 fragment due to TPE rotors, obtained by DFT calculations, allows interaction with guest molecules for chemical sensing.

Thermogravimetric Analysis

Thermogravimetric analyses (TGA) show that both NUS-24 bulk powder and nanosheets are thermally stable up to 400° C. Excellent chemical stability of bulk NUS-24 was also proven through soaking tests using water, hydrochloric acid (6 M), sulphuric acid (6 M), sodium hydroxide (8 M), and common organic solvents. The extremely high thermal and chemical stabilities make NUS-24 attractive for applications even under corrosive conditions.

Porosity

Permanent porosity of bulk NUS-24 was demonstrated by its $N_2$ sorption isotherm at 77 K, which exhibits a type I sorption behavior with a Brunauer-Emmett-Teller (BET) surface area of 335 $m^2$ $g^{-1}$ and a total pore volume of 0.378 $cm^3$ $g^{-1}$. Pore size distribution calculated using nonlocal density functional theory (NLDFT) reveals the presence of both micropores (around 14 Å) and mesopores (around 28 Å). However, the BET surface area of NUS-24 nanosheets decreases after exfoliation in different organic solvent such as acetone (100 $m^2$ $g^{-1}$), ethanol (162 $m^2$ $g^{-1}$), and acetonitrile (92 $m^2$ $g^{-1}$). The total pore volume of nanosheets is also smaller than that of its bulk powder (0.13, 0.20, and 0.13 $cm^3$ $g^{-1}$ after exfoliation in acetone, ethanol, and acetonitrile, respectively). Pore size distribution shows that the microporous characteristics almost disappear in the 2D nanosheets. This might be due to the disruption of the π-π stacking among layers by as-exfoliated nanosheets.

2D Structure

The 2D layered structure of NUS-24 bulk powder was confirmed by field-emission scanning electron microscopy (FE-SEM, FIG. 3a-b). The sheet-like morphology of an as-exfoliated NUS-24, supported on a porous anodic aluminum oxide (AAO) substrate was also observed using FE-SEM (FIG. 3c-d). High-resolution transmission electron microscopy (HR-TEM) reveals that the thin sheet-like layered structure of the 2D nanosheets is retained after the liquid-exfoliation process (FIG. 3e). Interestingly, although the NUS-24 bulk powder is mainly amorphous based on the PXRD result, a clear crystal lattice was observed in the exfoliated NUS-24 nanosheets by HR-TEM, indicating that NUS-24 has ordered orientations in few-layered microstructures (FIG. 3f-g).

In order to fully study the possible long range orders, 2D layered crystalline structures of AA stacking and AB stacking of NUS-24 were optimized with the density-functional tight-binding (DFTB+) method, incorporating dispersion interactions. Although the pore size distribution of AA stacking model (20.2 Å×36.9 Å) and AB stacking model (9.3 Å×14.0 Å) do not agree well with the experimental data of NUS-24 bulk, the total stacking energy of AA stacking (540.2 kcal $mol^{-1}$) is much lower than that of the AB stacking (1831.5 kcal $mol^{-1}$). In addition, after exfoliation, the pore size distribution of NUS-24 nanosheets only contain mesopores (around 28 Å), which is close to the AA stacking model. Based on the results disclosed herein, it is believed that NUS-24 may adopt AA stacking, although the possibility of slipped stacking cannot be completely ruled out. With the aid of the AA stacking model, it is shown that the two adjacent TPE rotors is around 3.7 Å apart between two layers, and are attracted through π-π stacking that restricts their possible motions. Based on this model, it may be concluded that the lattice fringe spacing of 0.45 nm measured from the HR-TEM of NUS-24 nanosheets originates from the (660) crystal plane of the optimized structure (FIG. 3h).

The 2D layered structure of NUS-24 was further confirmed by atomic force microscopy (AFM) investigation. The NUS-24 nanosheets exfoliated in acetone were transferred on silicon wafers and studied by AFM for their lamellar features (FIG. 3i-j). As demonstrated by the AFM analyses on a total of 322 sites, more than 90% of the exfoliated NUS-24 have sheet-like morphology with a thickness of 2-5 nm (FIG. 3m) and a rather broad lateral size distribution (1.0-10.0 μm), indicating three to six layers of NUS-24 nanosheets based on the optimized AA stacking modelling structure. On the other hand, exfoliation in acetonitrile and ethanol can also be easily identified with the thickness of 3-5 nm (FIG. 3k-l). Without wishing to be bound by theory, it is believed that the exfoliation and stabilization of NUS-24 nanosheets can be facilitated by the dynamics of the TPE rotors, which helps to weaken the interlayer π-π stacking and prevent the restacking of exfoliated nanosheets. Even after 60 days, NUS-24 nanosheets suspended in acetone, acetonitrile, or ethanol solutions still exhibited a homogeneous state with a thickness of 3-4 nm. Dynamic light scattering (DLS) tests indicate that the average size of these nanosheets is 529 nm in acetone, 404 nm in acetonitrile, and 657 nm in ethanol based on the Stokes-Einstein equation (FIG. 3n). In addition, the clear Tyndall effect of solutions containing exfoliated NUS-24 provides strong evidence for the colloidal ultrathin 2D nanosheets (FIG. 3o). Moreover, the nanosheets exhibit stronger fluorescence emission at 77 K compared to that at room temperature (FIG. 3p), suggesting the turn-on fluorescence emission caused by the freezing of TPE rotors at low temperatures. This phenomenon is reminiscent of aggregation-induced emission (AIE), in which turn-on fluorescence emission can be obtained by the restriction of molecular motions, which was confirmed by cryogenic differential scanning calorimetry (DSC). A distinct endothermic peak at −80° C. was observed in bulk NUS-24 during the heating scan, indicating a phase transition in which the frozen TPE molecular rotors become rotatable upon heating. The above characterization results strongly indicate NUS-24 has a 2D layered structure which can be exfoliated into nanosheets with liberated TPE molecular rotors that are suitable for further application.

Example 2: Use of NUS-24 in Chemical Sensing of VOCs

The dynamics of TPE rotors was demonstrated by size-selective VOC sensing. The experiments were performed by soaking NUS-24 nanosheets in various VOCs of different molecular size followed by photoluminescence tests.

Chemical Sensing of VOCs

The acetone suspension (40 µL) containing exfoliated NUS-24 nanosheets (0.1 mg mL$^{-1}$) was added into individual VOC solution (2 mL), which was thoroughly stirred before each photoluminescence measurement. Fluorescence spectra were recorded on a PTI/QM spectrophotometer. The excitation wavelength for liquid VOC sensing was 365 nm. The VOC analytes tested were: dichloromethane, chloroform, tetrahydrofuran, n-hexane, cyclohexane, benzene, toluene, o-xylene, m-xylene, p-xylene, 1,4-diisopropylbenzene, aniline and nitrobenzene.

Effect of Increasing Molecular Size on Relative Fluorescence Intensity

The NUS-24 nanosheets exhibit turn-on fluorescence after being soaked in VOCs, with rough positive correlations between the emission intensity of NUS-24 nanosheets and the molecular size of the VOCs tested. For example, the NUS-24 nanosheets exhibit a yellow emission in acetone, and the emission intensity increases with increasing molecular size of the VOC analytes, including dichloromethane, chloroform, tetrahydrofuran, n-hexane, cyclohexane, benzene, toluene, o-xylene, m-xylene, p-xylene and 1,4-diisopropylbenzene (FIG. 4a). Using the emission intensity of NUS-24 nanosheets in acetone ($I_{acetone}$) as the reference, the relative intensities ($I_R=I/I_{acetone}$) of NUS-24 nanosheets in other analytes are shown in FIG. 4e. 1,4-diisopropylbenzene (4.3×9.4 Å), which is the largest analyte, has the highest value of $I_R$ (4.40) among all the tested VOCs. Compared to NUS-24 nanosheets, the emission intensity increase of NUS-24 bulk powder soaking in VOCs is relatively weaker. This suggests a higher sensitivity for NUS-24 nanosheets compared to that of NUS-24 bulk powder, and this is believed to originate from the stronger interactions of liberated TPE rotors on the surface of NUS-24 nanosheets with analytes. It is worth noting that the different $I_R$ values between nanosheets ⊃ benzene (2.11) and nanosheets ⊃ toluene (2.61), which suggests that NUS-24 nanosheets can be used to discriminate benzene from toluene. This is of great importance in VOC sensing due to the different toxicity of these two compounds. In addition, NUS-24 nanosheets also demonstrate a good discrimination among xylene isomers (o-xylene/m-xylene/p-xylene), which is currently a big challenge in chemical sensing due to their similar structures and physicochemical properties. For example, the $I_R$ values of nanosheets ⊃ o-xylene, nanosheets ⊃ m-xylene, and nanosheets ⊃ p-xylene are 3.24, 2.80, and 3.77, respectively. In contrast, NUS-24 bulk powder exhibits poor discrimination as $I_R$ values of bulk ⊃ o-xylene (1.29), bulk ⊃ m-xylene (1.28), and bulk ⊃ p-xylene (1.34) indicating almost the same emission intensity (FIG. 4e). The control experiment indicates that the TPE-1 linker is unable to detect any VOCs, mainly because it is almost non-emissive in VOCs. It is believed that the exposed TPE rotors on the large surface of NUS-24 nanosheets create a more discriminating environment than the free TPE linkers, resulting in much-enhanced sensitivity and selectivity in chemical sensing.

Moreover, there is no obvious fluorescence peak shift in the turn-on process for analytes ranging from acetone to 1,4-diisopropylbenzene, suggesting no strong π-π stacking between NUS-24 nanosheets and VOC analytes. Therefore, the VOC sensing principle of NUS-24 nanosheets should mainly follow the AIE mechanism. Essentially, the fluorescence emission of NUS-24 nanosheets is positively proportional to the restriction of TPE rotors caused by interacting with VOC analytes. Larger analytes tend to interact more strongly with TPE rotors, resulting in stronger fluorescence emissions. Compared to the TPE rotors in 3D porous materials, the TPE rotors in NUS-24 nanosheets exhibit dynamic time-dependent behavior when interacting with VOC analytes. As can be seen in FIG. 4b, 15 min is required for the highest fluorescence emission to be reached after adding 20% of 1,4-diisopropylbenzene into acetone suspension containing NUS-24 nanosheets. This phenomenon is probably due to the weaker confinement effect of 2D nanosheets exerted onto the VOC analytes compared to that of the 3D porous materials. Hence, a longer time is required to reach equilibrium where maximum restriction on the dangling TPE rotors, as well as the highest fluorescence emission, is achieved. Moreover, the static nature of the turn-on process is also proven by consistent fluorescence lifetimes of NUS-24 nanosheets before and after adding VOCs. For example, the lifetimes ($\tau_0$) of nanosheets ⊃ acetone, nanosheets ⊃ n-hexane, nanosheets ⊃ benzene and nanosheets ⊃ 1,4-diisopropylbenzene were calculated to be 1.04, 1.11, 1.11 and 1.12 ns, respectively, by the biexponential fitting of the fluorescence emission decay data.

Turn-Off Fluorescence

Besides turn-on, the turn-off fluorescence mode was also observed in NUS-24 nanosheets using nitrobenzene as the analyte, which is well known for its ability in quenching fluorescence. We could clearly observe a huge blue shift (~60 nm) of the fluorescence peak from nanosheets (520 nm) to nanosheets ⊃ nitrobenzene (460 nm) (FIG. 4a), indicating that the turn-off process appears to be mainly caused by a donor-acceptor electron-transfer mechanism instead of the AIE mechanism observed in the turn-on process.

Effect of Increasing Analyte Concentration on Relative Fluorescence Intensity

To further investigate the effect of an analyte's molecular size on the restriction of dynamic TPE rotors, fluorescence titrations were carried out with gradual addition of a small amount of benzene (4.3×5.0 Å), naphthalene (5.0×6.7 Å), or phenanthrene (5.0×9.2 Å) to the acetone suspensions containing NUS-24 nanosheets. Fluorescence enhancement was also observed following the order of phenanthrene>naphthalene>benzene (see FIGS. 4c-d), agreeing well with the size effect elucidated previously. This gives a rare example of ultrathin 2D nanosheets containing molecular rotors with an almost perfect linear relationship between turn-on fluorescence and analyte concentration.

Example 3: Use of NUS-24 Nanosheets for the Chemical Sensing of Metal Ions

NUS-24 nanosheets were also screened for their capability in the chemical sensing of metal ions including transition metal ions ($Ag^+$, $Mn^{2+}$, $Co^{2+}$, $Ni^{2+}$, $Cu^{2+}$, $Zn^{2+}$, $Cd^{2+}$, $Pb^{2+}$, $Al^{3+}$, $Ga^{3+}$, $Fe^{3+}$, $Ln^{3+}$, and $Cr^{3+}$), alkali metal ions ($Li^+$, $Na^+$, and $K^+$), alkaline-earth metal ions ($Mg^{2+}$, $Ca^{2+}$, $Ba^{2+}$, and $Sr^{2+}$) and rare earth metal ions ($Ce^{3+}$, $Eu^{3+}$, $Tb^{3+}$, and $Er^{3+}$).

Titration experiments of metal ions were carried out by adding aliquots (10 μL) of metal salt solutions ($1.0 \times 10^{-2}$ M) into the acetone suspension (2 mL) containing NUS-24 nanosheets (0.1 mg mL) at intervals of 5 min. Fluorescence spectra were recorded after the addition of metal salt solutions. The excitation wavelength was 365 nm. The fluorescence quenching was analyzed using the Stern-Völmer equations derived for 1:1 complexes to determine the binding mode:

$$I_0/I = 1 + K_{sv}[Q] \quad (2)$$

High Sensitivity for $Fe^{3+}$ Ions

Among the metal ions tested, $Cu^{2+}$, $Co^{2+}$, $Mn^{2+}$ and $Fe^{3+}$ exhibit strong quenching effects. In particular, the emission intensity of NUS-24 nanosheets keeps decreasing with gradual addition of $Fe^{3+}$ (FIG. 5a), affording a linear relationship ($R^2$=0.9959) which agrees with the Stern-Völmer (S-V) equation and suggests a 1:1 stoichiometry of chemical sensing (FIG. 5b). $Fe^{3+}$ demonstrates the highest quenching percentage of 91.7%, while the quenching percentages of $Cu^{2+}$, $Co^{2+}$ and $Mn^{2+}$ are 54.1%, 51.1% and 41.4%, respectively. The quenching constant $K_{SV}$ represents the quenching sensitivity, and the $K_{SV}$ values were calculated to be 27214, 4387, 3242 and 1984 $M^{-1}$ for $Fe^{3+}$, $Co^{2+}$, $Cu^{2+}$ and $Mn^{2+}$, respectively. The quenching percentage of other metal ions were from 2% to 30% and the $K_{SV}$ were from 30 to 1200 $M^{-1}$ (FIG. 5e), which are all much lower than that of $Fe^{3+}$. This is probably because $Fe^{3+}$ contains unoccupied d orbitals and has a smaller diameter compared to other metal ions. Therefore, when the nanosheets interact with $Fe^{3+}$, the electrons can easily transfer from nanosheets to $Fe^{3+}$, leading to quick fluorescent quenching of the nanosheets.

Nanosheets Display Higher Sensitivity and Selectivity for $Fe^{3+}$ Over Bulk Powder In order to demonstrate the advantages of nanosheets for $Fe^{3+}$ sensing, several fluorescent molecules including TPE-1, TPE-2, tetraphenylethylene (TPE) and pyrene as well as NUS-24 bulk powder were chosen for comparison. Clearly, the NUS-24 nanosheets can be quenched faster than the small fluorescent molecules and NUS-24 bulk powder (FIG. 5b). The $K_{SV}$ values were calculated to be 27214, 10617, 3632, 2296, 2011, and 1659 $M^{-1}$ for NUS-24 nanosheets, NUS-24 bulk powder, TPE, pyrene, TPE-1, and TPE-2, respectively (FIG. 5c). In addition, three other metal ions including $Cu^{2+}$, $Mn^{2+}$, and $Co^{2+}$ were also tested. NUS-24 nanosheets display a higher sensitivity in sensing the selected metal ions in comparison to NUS-24 in bulk powder form and the small fluorescent molecules TPE-1, TPE-2, TPE and pyrene. The superior sensitivity of NUS-24 nanosheets can be attributed to their fully exposed external surface area allowing sufficient contact and interaction with analytes. Lastly, ion selectivity was determined using $K_{sv}$ ($Fe^{3+}$)/$K_{sv}$($Mn^{2+}$) and $K_{sv}$($Fe^{3+}$)/$K_{sv}$($Cu^{2+}$). As shown in FIG. 5d, NUS-24 nanosheets show a much higher selectivity toward $Fe^{3+}$ than the four small fluorescent molecules as well as the bulk powder, indicating the advantage of nanosheets for metal ion sensing.

Inspired by the high sensitivity and selectivity of NUS-24 nanosheet toward $Fe^{3+}$, which plays a significant role in many biochemical processes such as oxygen metabolism and synthesis of DNA and RNA, the trace amount sensing of $Fe^{3+}$ using NUS-24 nanosheets was studied. The apparent quenching constant $K_q$ ($K_q = K_{SV}/\tau_0$)[66] for NUS-24 nanosheets quenched by $Fe^{3+}$ was evaluated to be $2.62 \times 10^{13}$ $M^{-1}$ $s^{-1}$, which is three orders of magnitude higher than that of conventional bimolecular quenching systems (~$10^{10}$ $M^{-1}$ $s^{-1}$) (Olley, D. A. et al. *Chem. Mater.* 23, 789-794 (2011).). In addition, NUS-24 nanosheets can detect $Fe^{3+}$ at very low concentrations by fluorescence quenching. The detection limit (Hu, Y. et al. *Chem. Commun.* 52, 5734-5737 (2016)) ($3\sigma/K_{SV}$, $\sigma$ is the standard deviation of this detection method) of $Fe^{3+}$ was calculated to be $9 \times 10^{-4}$ M. In order to further understand the quenching details, this process was examined by time-resolved fluorescence measurements. The lifetimes of NUS-24 nanosheets remained almost unchanged before and after adding $Fe^{3+}$ (1.04 vs 1.09 ns, the right inset of FIG. 5e), suggesting a static nature for the fluorescence quenching. Furthermore, the fluorescence quenching of NUS-24 nanosheets by $Fe^{3+}$ can be easily seen from the fluorescence microscopy images (the left inset of FIG. 5e), implying the potential applications of NUS-24 nanosheets in naked-eye detection of $Fe^{3+}$.

Example 4: Mixed Matrix Membranes Containing NUS-24 Nanosheets

NUS-24 nanosheets were incorporated into mixed matrix membranes (MMMs) in order to further understand the effect of TPE rotors in practical sensing applications, especially the turn-on fluorescence for VOC sensing. Poly(ethylene imine) (PEI) was chosen as the polymeric matrix for the preparation of MMMs because of the lack of electron-deficient groups that minimizes interference with the fluorescence emission of NUS-24 nanosheets.

MMMs were fabricated by casting stock solutions containing fully dissolved polymers (PEI) and suspended NUS-24 nanosheets according to Kang, Z. et al. *Chem. Mater.* 28, 1277-1285 (2016). In a typical process, an acetone suspension (2.5 mL) containing exfoliated NUS-24 nanosheets (0.1 mg/mL) was sonicated for 30 min using an ultrasonic homogenizer (Biobase, JY92-IIDN) followed by stirring for another 120 min. This cycle was repeated three times, and then PEI (200 mg) dissolved in ethanol (2.5 mL) was added followed by another sonication-stirring cycle to give the membrane casting solution, which was cast onto a flat glass substrate followed by slow vaporization of the solvent to give the final MMMs.

FE-SEM, Energy-dispersive X-ray spectroscopy (EDX) elemental mapping and XPS spectra indicate the pure organic composition of MMMs containing only carbon and nitrogen elements (FIG. 6a-b). The thickness of the membrane was estimated to be around 40 μm from the cross-sectional SEM image (FIG. 6c). A flat and smooth surface of the membrane was confirmed by AFM (FIG. 6f). The uniform yellow fluorescence emission of the membrane suggests a homogeneous dispersion of NUS-24 nanosheets within the PEI matrix (FIG. 6d-e).

MMMs were exposed to various VOC vapors (benzene, toluene, styrene and chlorobenzene) and their fluorescence emission ($\lambda_{ex}$=365 nm, $\lambda_{em}$=530 nm) was checked. The procedure for the chemical sensing of VOC vapours and metal ions using MMMs is as follows: The MMM (1×1 cm) was fixed into the inner surface of a quartz cuvette, which was placed into the saturated VOC vapours or metal salt solutions (2 mL, 1×10$^3$ M in aqueous solution) for 5 min followed by a photoluminescence test ($\lambda_{ex}$=365 nm, $\lambda_{em}$=530 nm). The quenching percentage was estimated using the formula $(I_0-I)/I_0 \times 100\%$, where $I_0$ is the original maximum peak intensity and I is the maximum peak intensity after exposure to VOC vapours or metal ion solutions.

Results

There was barely any turn-on fluorescence observed after 5 min exposure to VOC vapors (fluorescence enhancement <5%, FIG. 6g-h), confirming the restriction of TPE rotors by PEI matrix which leads to reduced sensitivity toward VOC sensing based on turn-on fluorescence. On the other hand, it is possible that the polymeric matrix works as a barrier to slow down the diffusion of VOC molecules leading to poor interactions with NUS-24 nanosheets and accordingly weaken turn-on fluorescence. To rule out this possibility, MMMs were exposed to the vapors of fluorescence-quenching compounds including nitromethane, nitrobenzene, 2-nitrotoluene and 2,4,6-trinitrophenol (picric acid). Dramatic fluorescence quenching of MMMs was observed in 1 min, indicating that the barrier effect imposed by PEI matrix, if there is any, should not be the major reason for the attenuated turn-on fluorescence in MMM-based VOC sensing.

It was noticed that 2,4,6-trinitrophenol exhibited the fastest quenching rate within the initial 1 min among all the fluorescence-quenching compounds (FIG. 6g-h). This can be attributed to its three electron-withdrawing nitro groups that strongly quench the fluorescence through a donor-acceptor electron-transfer mechanism. However, the quenching process caused by 2,4,6-trinitrophenol saturated after 1 min, which may be due to the hydrogen bonding interaction between the —OH groups of 2,4,6-trinitrophenol and the —NH— groups of PEI, preventing further penetration of 2,4,6-trinitrophenol into the membranes. On the contrary, nitrobenzene, with a smaller molecular size and lack of hydrogen bonding interaction, could continuously quench the fluorescence emission of MMMs over the whole test period (5 min). After 5 min, the quenching percentage obtained using nitrobenzene is 41.5%, which is much higher than that obtained using 2,4,6-trinitrophenol (27.0%), 2-nitrotoluene (15.2%), and nitromethane (10.6%). These results suggest that MMMs containing NUS-24 nanosheets can be used for the detection of explosives which are mainly nitro-containing compounds.

The MMMs were further used for the chemical sensing of metal ions in aqueous solutions. As shown in FIG. 6i, $Fe^{3+}$ also exhibits the fastest quenching speed among all the metal ions being tested. After 1 min of soaking MMMs in metal ion solutions, the quenching percentages are 28.4%, 12.0% and 8.9% for $Fe^{3+}$, $Cu^{2+}$ and $Co^{2+}$, respectively, while the other metal ions are all less than 7% (FIG. 6j).

NUS-24 Summary

In summary, TPE molecular rotors were introduced into 2D porous organic nanosheets (NUS-24) for fluorescence-based chemical sensing. Compared to NUS-24 bulk powder, the exfoliated NUS-24 nanosheets exhibit stronger turn-on fluorescence upon contact with electron-rich VOCs, and the fluorescence enhancement is positively correlated with the molecular size of VOC molecules. This can be attributed to the restriction of liberated TPE rotors on the external surface of NUS-24 nanosheets when interacting with VOC molecules, which is similar to the AIE mechanism. The proposed mechanism was further proven by incorporating NUS-24 nanosheets into PEI affording MMMs, by which the TPE rotors can be almost completely restricted by the polymeric matrix resulting in greatly attenuated turn-on fluorescence upon exposure to VOC vapours. Nevertheless, the NUS-24 nanosheets and MMMs exhibit practical sensing capability toward nitro-containing compounds and $Fe^{3+}$ ion through fluorescence quenching caused by donor-acceptor electron-transfer mechanism. These results demonstrate the promising application of NUS-24 in explosive detection and in environmental monitoring.

Example 5: Synthesis and Characterization of NUS-25

Synthesis of NUS-25 Bulk Powder

NUS-25 bulk powder was synthesized using Suzuki-Miyaura coupling reactions. Briefly, a mixture of 1,2-diphenyl-1,2-bis(4-(4,4,5,5-tetramethyl-1,3,2-dioxaborolan-2-yl)phenyl)ethane (monomer-1: 351 mg, 0.6 mmol), hexabromophenylbenzene (monomer-2: 202 mg, 0.2 mmol), $K_2CO_3$ (442.5 mg, 3.2 mmol) and $Pd(PPh_3)_4$ (11.6 mg, 0.01 mmol) in DMF/water (16 mL/2 mL) was degassed and purged with $N_2$. The mixture was stirred at 150° C. for 72 h and then cooled to room temperature and poured into water. The precipitate was collected by filtration, repeatedly rinsed with hydrochloric acid (2 M), water, tetrahydrofuran, ethanol, dichloromethane, acetone, and then rigorously washed by Soxhlet extraction for 24 h with each of chloroform, tetrahydrofuran and acetone sequentially, and finally dried in vacuum to give NUS-25 (298 mg, 95% yield) as green powder.

Preparation of NUS-25 Ultrathin 2D Nanosheets

NUS-25 nanosheets were prepared from NUS-25 bulk powder by ultrasonic exfoliation in organic solvents (FIG. 7a). Briefly, 5 mg of the NUS-25 bulk powder sample was suspended in 10 mL of acetonitrile solvent, and was sonicated with a frequency of 40 kHz for 4 h to give a homogeneous dispersion. The resulting dispersion was centrifuged at 4000 rpm for 10 min. The supernatant was collected and followed by another centrifugation at 10000 rpm for 10 min to further remove non-exfoliated powder.

Characterization of NUS-25 Nanosheets

As schematically illustrated in FIG. 7, NUS-25 bulk powder was constructed using 1,2-diphenyl-1,2-bis(4-(4,4,5,5-tetramethyl-1,3,2-dioxaborolan-2-yl)phenyl)ethane (monomer-1) and hexakis(4-bromophenyl)benzene (monomer-2) with a yield of 95% (see above for details). A wide range of solvents with different surface tensions were screened, and it was found that acetonitrile was a best suited of the solvents tested to exfoliate NUS-25 bulk powder into ultrathin 2D nanosheets (FIG. 8a).

Morphology

The morphology of the bulk and nanosheet forms of NUS-25 were studied by field-emission scanning electron microscopy (FE-SEM), high-resolution transmission electron microscopy (HR-TEM), and atomic force microscopy (AFM). NUS-25 bulk powder exhibits a layered stacking morphology from the FE-SEM images (FIG. 8c). The as-exfoliated NUS-25 nanosheets, deposited on a porous anodic aluminum oxide (AAO) substrate, exhibit flat morphology with small thickness highlighting their 2D features (FIG. 8d-e). HR-TEM images confirm the ultrathin graphene-like morphology of NUS-25 nanosheets as compared to the bulk powder (FIG. 8g-h). Although NUS-25 bulk powder is generally amorphous due to the irreversibility of C—C coupling reaction, crystal lattices can still be identified in the HR-TEM images of NUS-25 nanosheets (FIG.

8*i-j*), indicating their partial crystallinity in small domains. Fast Fourier transform (FFT) of the crystal lattices results in diffraction spots that can be attributed to the ordered orientation in few-layered microstructures (FIG. 8*j*). In order to fully understand the possible long-range orders, a simulated eclipsed AA stacking structure of NUS-25 was optimized to remove geometric distortions. It is worth noting that the experimental lattice distance is around 0.4 nm, matching well with the (−550) planes of the modeled AA stacking structure (inset of FIG. 8*j*).

The molecular-level understanding of the ultrathin 2D nanostructure was further confirmed by AFM investigations. A flat and graphene-like morphology for NUS-25 nanosheets was observed on silicon wafers (FIG. 8*k-l*). The average thickness of NUS-25 nanosheets was around 3.0 nm, corresponding to four-layered structures based on optimized AA stacking model (inset of FIG. 8*l*). Notably, the lateral size of NUS-25 nanosheets ranges from 2 μm to 20 μm (FIG. 8*k*), leading to aspect ratios higher than 1000, thereby confirming their 2D layered features. Based on dynamic light scattering (DLS) data, the average size of NUS-25 nanosheets is around 4 μm in acetonitrile solution, matching well with the FE-SEM, HR-TEM and AFM results. Furthermore, the suspension of NUS-25 nanosheets in acetonitrile exhibits a typical Tyndall effect (FIG. 8*n*), indicating the colloidal feature of the freestanding and homogeneous ultrathin 2D nanosheets. Impressively, NUS-25 nanosheets can exhibit a homogeneous state in acetonitrile suspension without agglomeration even after 30 days, which may be attributed to the nonplanar TPE rotors that can weaken the interlayer π-π stacking and prevent the re-stacking of exfoliated nanosheets.

Spectral Analysis

Fourier transform infrared spectroscopy (FT-IR) spectra show almost complete disappearance of the C—Br vibrations (around 530 $cm^{-1}$) in both bulk and nanosheets of NUS-25. X-ray photoelectron spectroscopy (XPS) spectra also suggest the removal of Br element in NUS-25 (Brls: 70.4 eV, FIG. 9*a*). These results confirm the completion of the cross-coupling reaction.

Raman spectra of bulk and nanosheets of NUS-25 indicate nearly identical main peaks located at around 1589 $cm^{-1}$, which can be assigned to the carbon vibration of $sp^2$ hybridization. However, the NUS-25 nanosheets exhibit a slight shift toward high wavenumber (1592 $cm^{-1}$) compared to the bulk powder, indicating their structural relaxation arising from small thickness (FIG. 9*b*).

The ultraviolet-visible (UV-Vis) spectrum of NUS-25 nanosheets shows a large blue shift of about 32 nm compared to that of bulk powder (370 nm vs 338 nm), which can be attributed to the reduced π-π interactions caused by the exfoliation (FIG. 9*c*). To further prove this point, UV-Vis diffuse reflectance measurement was conducted for understanding the changes of optical band gap ($E_g$) between the bulk powder and the 2D nanosheets. As shown in FIG. 9*d*, the corresponding $E_g$ of NUS-25 bulk powder was calculated to be 2.56 eV. After exfoliation, the $E_g$ increases to 3.02 eV for NUS-25 nanosheets, confirming the reduction of such π-π stacking interactions observed in UV-Vis spectra. It is noted that the fluorescent emission of NUS-25 nanosheets exhibits a blue shift of about 12 nm compared to that of NUS-25 bulk (508 nm vs 496 nm, FIG. 8*f* and FIG. 9*e*), further demonstrating the structural relaxation of the as-exfoliated ultrathin nanosheets. Moreover, the observed emission colours of monomer-1 (blue) and NUS-25 nanosheets (green) are differentiable on the Commission Internationale de L'Eclairage (CIE) chromaticity diagram (FIG. 9*f*).

Electronic Structure Calculations

To provide an insight into the spectroscopic characterization of NUS-25 nanosheets, density functional theory (DFT) calculations were performed to examine the electronic structures of NUS-25 (FIG. 9*g*). To quantitatively evaluate the interactions between NUS-25 and PAH molecules, the electronic properties of a NUS-25 fragment were calculated using DFT. Initially, the structure of NUS-25 was optimized by Forcite using Materials Studio to remove geometric distortions. Then, an NUS-25 fragment with a complete ring containing all typical building blocks was used in DFT calculations. The cleaved bonds of the ring were terminated by hydrogen atoms. The nine PAH molecules were optimized using the B3PW91 functional with 6-31G(d) basis set. The HOMO and LUMO energy levels of the NUS-25 fragment and PAH molecules were calculated using the B3PW91 functional with 6-311G** basis set.

The calculated frontier orbitals indicate that they maintain the characteristics of their individual components due to the absence of any electron-withdrawing group in NUS-25 framework, which is beneficial for highly fluorescent emission. For NUS-25 nanosheets, the main adsorption band locates at around 338 nm, corresponding to the HOMO to LUMO transition. In addition, thermogravimetric analysis (TGA) and chemical stability test indicate extremely high stability of both bulk and nanosheets of NUS-25, ensuring their applications even under corrosive conditions.

Porosity

The permanent porosity of NUS-25 bulk powder was demonstrated by $N_2$ sorption isotherm at 77 K. Type I sorption behavior was observed with a Brunauer-Emmett-Teller (BET) surface area of 623 $m^2$ $g^{-1}$ and a total pore volume of 0.69 $cm^3$ $g^{-1}$. The pore size distribution calculated using nonlocal density functional theory (NLDFT) reveals nanopores at around 12.6 Å. However, the BET surface area of NUS-25 nanosheets clearly decreases after exfoliation in acetonitrile solution (184 $m^2$ $g^{-1}$). This might be due to the disruption of the π-π stacking among the layers by exfoliation process. Both bulk powder and nanosheets of NUS-25 show no obvious shift of diffraction peaks in powder X-ray diffraction (PXRD) patterns, indicating the amorphous nature of NUS-25. Despite its amorphous feature, a crystalline model of NUS-25 was simulated considering the most possible connections and lowest total packing energy. From the simulated structure, the distance between two adjacent layers of NUS-25 is about 6.8 Å. Furthermore, it was found that the total stacking energy of AA stacking (356 kcal $mol^{-1}$) is significantly lower than that of the AB stacking (4642 kcal $mol^{-1}$). Give the above facts, it is believed that NUS-25 may adopt AA stacking model to minimize interlayer repulsion, although the possibility of slipped stacking cannot be completely ruled out. Notably, with the aid of AA stacking model, there is barely any room for the molecular motions of TPE rotors in NUS-25 due to the strong confined steric hindrance. Static TPE rotors can prevent nonradiative decay and afford high fluorescent emission that is reminiscent of the AIE mechanism.

Fluorescence

The size-dependent turn-on fluorescence emission of NUS-25 nanosheets was evaluated. The experiments were performed by suspending NUS-25 nanosheets in various VOCs of different molecular size, followed by photoluminescence tests. The acetonitrile suspension (200 μL) containing exfoliated NUS-25 nanosheets (0.1 mg $mL^{-1}$) was added into individual VOC solutions (1.8 mL), which was thoroughly stirred before each photoluminescence measurement. Fluorescence spectra were recorded on a PTI/QM spectrophotometer. The excitation wavelength for liquid VOC sensing was 365 nm.

NUS-25 nanosheets display turn-on fluorescence emissions in the presence of VOCs. However, it is difficult to conclude any positive correlation between the emission intensity and the molecular size of the VOCs. The emission intensity of NUS-25 nanosheets in n-hexane ($I_{n\text{-}hexane}$) is used as the reference, and the relative intensities ($I_R=I/I_{n\text{-}hexane}$) of NUS-25 nanosheets in other VOCs can be calculated as shown in FIG. 10a. The $I_R$ values of nanosheets⊃benzene (4.3×5.0 Å) and nanosheets⊃1,4-diisopropylbenzene (4.3×9.4 Å) are only 1.04 and 1.15, respectively, which are much lower than the values obtained in NUS-24 nanosheets containing free TPE rotors (1.24 for nanosheets⊃benzene and 4.40 for nanosheets⊃1,4-diisopropylbenzene). In addition, there is no obvious fluorescence peak shift for these analytes ranging from n-hexane to 1,4-diisopropylbenzene, suggesting no strong π-π interactions caused by electron transfer between the nanosheets and VOC analytes. The emission intensity ratios of POFs in benzene versus those in n-hexane ($I_B=I_{benzene}/I_{n\text{-}hexane}$), and POFs in 1,4-diisopropylbenzene versus those in n-hexane ($I_D=I_{1,4\text{-}diisopropylbenzene}/I_{n\text{-}hexane}$) can be used to evaluate the dynamic degree of the TPE rotors. High emission intensity ratios indicate high dynamic degree of the TPE rotors due to inhibition of the rotation/vibration of these TPE rotors to block nonradiative decay. As shown in FIG. 10b, NUS-22 and NUS-23 containing large cavity size with high dynamic degree of TPE rotors have higher $I_B$ and $I_D$ values than others [4.66 ($I_B$) and 9.62 ($I_D$) for NUS-22, 3.94 ($I_B$) and 5.95 ($I_D$) for NUS-23]. In addition, the $I_B$ value of our reported 2D MOF (NUS-1) containing TPE rotors is 2.78. Again, NUS-25 has the lowest $I_B$ (1.04) and $I_D$ (1.15) values among all the POFs being tested. It is believed there is a conformational lock effect imposed on the TPE rotors in NUS-25 confined porous nanosheets, leading to size insensitivity for VOCs sensing. Although the size-selective turn-on sensing is absent in NUS-25 nanosheets, the turn-off characteristic is still obvious when nitrobenzene was used as the analyte. Fluorescence titration was conducted by gradually adding trace amounts of nitrobenzene to NUS-25 nanosheets in acetonitrile solutions, and the quenching constant $K_{SV}$ was calculated to be 749910 $M^{-1}$ (FIG. 12b), which is much higher than that of NUS-24 2D nanosheets (373740 $M^{-1}$), indicating easy electron transfer from NUS-25 nanosheets to particular analytes for chemical sensing applications.

Example 6: Use of NUS-25 in Chemical Sensing

The highly fluorescent emission of NUS-25 nanosheets with ultrathin thickness inspired the exploration of their potential in molecular recognition and chemical sensing via π-π interactions, specifically the molecular recognition of polycyclic aromatic hydrocarbons (PAH molecules), which are major sources of air pollutants. In addition, some of them (e.g., acenaphthylene, pyrene and benzo[a]pyrene) can be classified as carcinogens.

Titration experiments of PAHs were carried out by adding aliquots of PAHs solutions (120 μL triphenylene: 0.25 M in $CH_2Cl_2$; 300 μL chrysene: 0.1 M in $CH_2Cl_2$; other PAHs (60 μL) were 0.5 M in $CH_2Cl_2$) into an acetonitrile suspension (2 mL) containing NUS-25 nanosheets (60 μg $mL^{-1}$) at intervals of 5 min. Titration experiments of $C_{60}$ and $C_{70}$ were carried out by adding 90 μL aliquot solutions ($5\times10^{-4}$ M in toluene) into a 2 mL acetonitrile suspension containing NUS-25 nanosheets (60 μg $mL^{-1}$) at intervals of 5 min. Fluorescence spectra were recorded after the addition of PAHs solutions. The excitation wavelength was 365 nm. The fluorescence quenching was analyzed using the Stern-Völmer equations derived for 1:1 complexes to determine the binding mode:

$$I_0/I=1+K_{sv}[Q] \qquad (2)$$

The quenching percentage was estimated using the formula $(I_0-I)/I_0\times100\%$, where $I_0$ is the original maximum peak intensity and I is the maximum peak intensity after exposure to PAHs solutions.

Selectivity Towards Sensing for Acenaphthylene Over Other PAHs

As can be seen in FIG. 11a, a significant decrease of fluorescence emission intensity of NUS-25 nanosheets was observed by gradual addition of acenaphthylene, a toxic PAH compound. Notably, there are obvious blue shifts in fluorescence peaks of NUS-25 nanosheets during the quenching processes triggered by the titration of acenaphthylene (~10 nm) and pyrene (~13 nm). In addition, the peak position and shape of the UV-Vis spectra of host-guest binding (acenaphthylene binds with NUS-25 nanosheets) also changed gradually (red-shift) during titration. All these results suggest strong π-π interactions between NUS-25 nanosheets and acenaphthylene, which is different from the previous reported NUS 20-24 with turn-on fluorescence for VOC recognition. The quenching percentage (QP) (see Dong, J.; Zhou, Y.; Zhang, F.; Cui, Y. Chem.—Eur. J. 2014, 20, 6455-6461; Pramanik, S.; Zheng, C.; Zhang, X.; Emge, T. J.; Li, J. J. Am. Chem. Soc. 2011, 133, 4153-4155) caused by the addition of acenaphthylene was calculated to be 93.4%, which was much higher than that of other PAHs being tested in this study including pyrene (26.0%), phenanthrene (14.4%), fluorene (12.4%), triphenylene (8.4%), chrysene (7.9%), naphthalene (6.7%), indene (6.6%), and benzene (4.0%). Furthermore, the measured absorbance $I_0/I$ at 495 nm varies as a function of PAHs concentration [mM] in a linear relationship ($R^2>0.99$), suggesting 1:1 stoichiometry of the interaction between acenaphthylene and NUS-25 nanosheets (FIG. 11b). The quenching constant ($K_{SV}$) representing the binding affinity was calculated to be 856.4 $M^{-1}$ for acenaphthylene, which is much higher than that of other PAHs ($K_{SV}$: 3.1-30.1 $M^{-1}$, FIG. 11c). In addition, the selectivities [$K_{sv}$(acenaphthylene)/$K_{sv}$(PAHs)] were calculated ranging from 28.5 to 276.3, indicating both high sensitivity and selectivity of NUS-25 nanosheets toward the chemical sensing of acenaphthylene. The apparent quenching constant $K_q$ ($K_q=K_{SV}/T_0$, $T_0$ is lifetime) was evaluated to be $3.53\times10^{11}$ $M^{-1}s^{-1}$ for acenaphthylene, which is higher than that of conventional bimolecular quenching systems (~$10^{10}$ $M^{-1}$ $s^{-1}$). Furthermore, the fluorescence quenching of NUS-25 nanosheets by acenaphthylene can be easily identified from the fluorescence microscopy images (FIG. 11h), implying the potential applications of NUS-25 nanosheets in naked-eye detection of toxic PAHs, especially acenaphthylene.

Selectivity Towards Sensing for $C_{70}$ Over $C_{60}$

The molecular recognition of $C_{60}$ and $C_{70}$ is a great challenge due to their similar molecular size and physical properties. Because of their rich π electrons, they were also employed as the analytes to see if their molecular recognition can be achieved using NUS-25 nanosheets based on responsive fluorescence. Both $C_{60}$ and $C_{70}$ can quench the fluorescence of NUS-25 nanosheets (FIG. 11d), but to a different extent. The QPs of $C_{60}$ and $C_{70}$ were calculated to be 44.7% and 83.6%, respectively, on the basis of titration experiments (FIG. 11e). NUS-25 nanosheets demonstrate a much higher binding affinity toward $C_{70}$ ($K_{SV}$: 212444 M$^{-1}$) over $C_{60}$ ($K_{SV}$: 37778 M$^{-1}$), with a selectivity [$K_{SV}(C_{70})$/$K_{SV}(C_{60})$] of 5.62 (FIG. 11f). In addition, a blue-shift of 4 nm was observed in the quenching process by $C_{70}$ (FIG. 11d), while a red-shift of 6 nm was observed in the case of $C_{60}$. Moreover, the UV-Vis spectra of the titration process also suggested the different π-π interaction between the NUS-25 nanosheets and $C_{70}$ or $C_{60}$. Without wishing to be bound by theory, the above data suggest different binding behaviour in photoinduced electron transfer (PET) that can be used for the molecular recognition of $C_{60}$ and $C_{70}$.

Chemical Sensing of Nitrobenzene

Fluorescence titration was conducted by gradually adding trace amounts of nitrobenzene to NUS-25 nanosheets in acetonitrile solutions (FIG. 12a). For NUS-25 nanosheets, the measured $I_0/I$ varies linearly with nitrobenzene concentration ($R^2$>0.99), and the quenching constant $K_{SV}$ was calculated to be 749910 M$^{-1}$ (FIG. 12b), indicating easy electron transfer from NUS-25 nanosheets to particular analytes for chemical sensing applications.

NUS-25 Bulk Powder Vs NUS-25 Nanosheets for Sensing

The behaviour between NUS-25 bulk powder and NUS-25 nanosheets were compared in the molecular recognition of PAHs. NUS-25 bulk exhibits much slower fluorescence quenching than NUS-25 nanosheets upon titration with acenaphthylene, $C_{70}$, and $C_{60}$. The $K_{SV}$ values of NUS-25 bulk powder were calculated to be 146.4 M$^{-1}$ for acenaphthylene (NUS-25 nanosheets: 856.4 M$^{-1}$), 60008 M$^{-1}$ for $C_{70}$ (NUS-25 nanosheets: 212444 M$^{-1}$), and 29256 M$^{-1}$ for $C_{60}$ (NUS-25 nanosheets: 37778 M$^{-1}$). Moreover, the selectivity [$K_{SV}(C_{70})$/$K_{SV}(C_{60})$] of NUS-25 bulk powder is also lower than that of NUS-25 nanosheets (2.05 vs 5.62). All these results strongly indicate that NUS-25 nanosheets is more sensitive and selective than its stacked bulk powder in the molecular recognition of PAHs. This feature can be attributed to the fully exposed surface in NUS-25 nanosheets allowing sufficient contact and interaction with PAHs for host-guest electron transfer.

In order to further compare NUS-25 nanosheets with other 3D POFs and 2D nanosheets with free dangling TPE rotors, the molecular recognition of acenaphthylene by NUS 20-24 was tested through titration experiments. Again, both the quenching percentages and the $K_{SV}$ constants indicate that NUS-25 nanosheets are more sensitive than all other materials (FIG. 11g). For example, the $K_{SV}$ constant of NUS-25 nanosheets is 5.98-fold that of 3D NUS-20 (143.1 M$^1$), and 3.49-fold that of NUS-24 2D nanosheets (245.4 M$^1$). In particular, it was clearly observed that the fluorescence emission of NUS-23 can only be slightly quenched by acenaphthylene ($K_{sv}$: 41.9 M$^{-1}$, which is only 4.9% of that of NUS-25 nanosheets). All the results suggest that the partial restricted TPE rotors in NUS-25 nanosheets are beneficial for π-π interactions with PAHs, which is possibly due to the smaller dynamics of the 2D nanosheet surface that would encourage stronger π-π interactions with PAH molecules through highly effective electron transfer.

NUS-25 Summary

In summary, there is provided a novel ultrathin 2D graphene-like nanosheets named NUS-25 which contain phenyl-rings as TPE molecular rotors with a thickness of around 2-5 nm. Their molecular structure was analyzed by Raman spectroscopy, FE-SEM, HR-TEM, and AFM. Benefiting from this special behavior, NUS-25 nanosheets exhibit a strong fluorescence emission that can be effectively and selectively quenched by acenaphthylene among a series of PAHs, making NUS-25 nanosheets an effective chemical sensor for acenaphthylene. Such a special sensitivity can be attributed to the ultrathin 2D feature of NUS-25 nanosheets, leading to strong interactions with acenaphthylene with photoinduced electron transfer behaviour.

The invention claimed is:

1. A polymer having a repeating unit according to Formula (IV):

(IV)

wherein E represents a central portion of the polymeric repeating unit and is represented by formula (V):

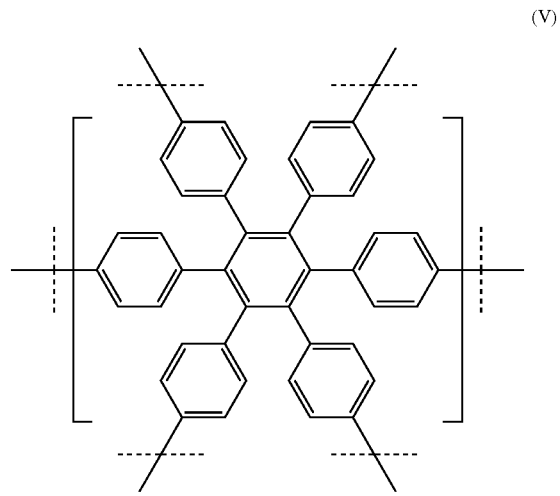

(V)

wherein the dotted lines relate to points of attachment to G; and wherein each G represents a peripheral portion of the polymeric repeating unit and is represented

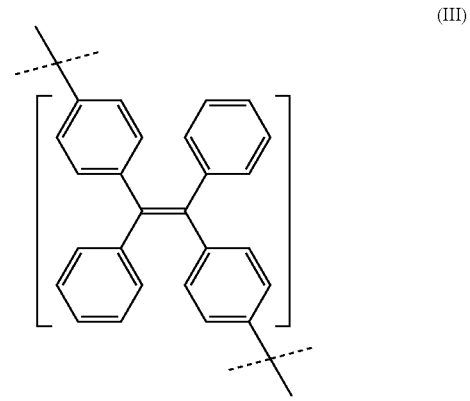

(III)

by formula (III):

wherein the dotted lines relate to points of attachment to unit E.

2. The polymer of claim 1, having the repeating unit of formula (IV), wherein the polymer is provided as a bulk polymer, optionally wherein the bulk polymer further has one or more of the following properties:
   (a) a Brunauer-Emmet-Teller (BET) surface area of from 450 to 750 $m^2\ g^{-1}$;
   (b) a total pore volume of from 0.5 to 0.9 $cm^3\ g^{-1}$; and
   (c) pores having a diameter of from 5 to 17 Å.

3. The polymer of claim 1, having the repeating unit of formula (IV), wherein the polymer is provided as a nanosheet, wherein the nanosheet has from one to four layers of the polymer, optionally wherein the nanosheet has one or more of the following properties:
   (a) a Brunauer-Emmet-Teller (BET) surface area of from 150 to 300 $m^2\ g^{-1}$;
   (b) a sheet size of from 2 to 20 μm when measured in an organic solvent by dynamic light scattering; and
   (c) a thickness of from 2 to 5 nm.

4. A method of preparing the polymer of claim 1, having the repeating unit of formula (IV), comprising reacting a compound of formula (VIII):

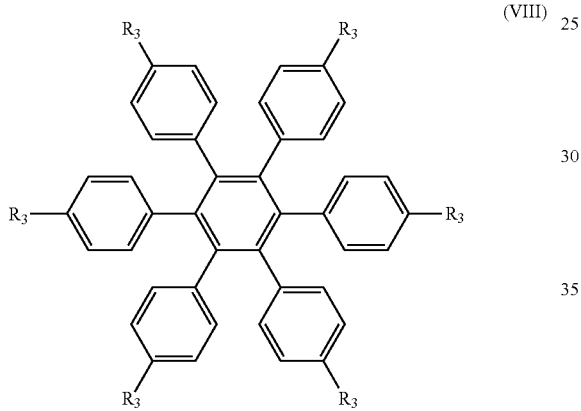

(VIII)

wherein $R_3$ represents halo, with a compound of formula (IX):

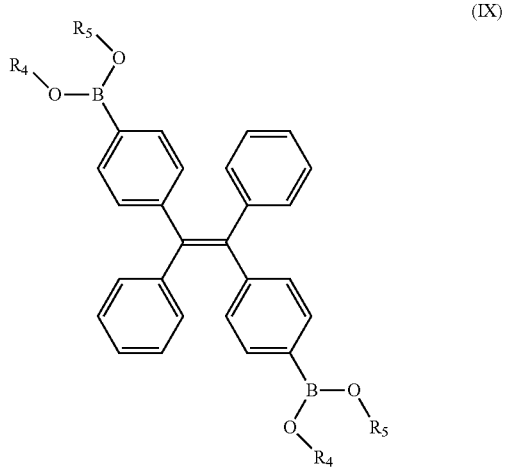

(IX)

wherein $R_4$ and $R_5$ independently represent $C_{1-6}$ alkyl, or $R_4$ and $R_5$ together with the boron and oxygen atoms to which they are attached form a 5- to 6-membered ring, of which, the latter two groups are unsubstituted or are substituted with from one to four substituents selected from $C_{1-6}$ alkyl.

5. The method of claim 4, further comprising
   forming the polymer having the repeating unit of formula (IV) into a bulk polymeric form; and
   exfoliating the bulk polymeric form to provide a nanosheet, wherein the nanosheet has from one to four layers of the polymer having the repeating unit of formula (IV).

6. A chemical sensor comprising the polymer of claim 1, having the repeating unit of formula (IV), optionally wherein the polymer is provided as a bulk polymer or as a nanosheet, wherein the nanosheet has from one to four layers of the polymer.

7. A method of detecting a volatile organic compound and/or an explosive compound and/or a polycyclic aromatic hydrocarbon with the chemical sensor as recited in claim 6, comprising
   exposing the chemical sensor to an analyte to detect the volatile organic compound by turn-on fluorescence; or
   exposing the chemical sensor to an analyte to detect the explosive compound or the polycyclic aromatic hydrocarbon by turn-off fluorescence in a quantitative manner or in a qualitative manner, optionally wherein:
   (a) the volatile organic compound is selected from one or more of the group consisting of dichloromethane, chloroform, tetrahydrofuran, n-hexane, cyclohexane, benzene, toluene, o-xylene, m-xylene, p-xylene, 1,4-diisopropylbenzene, and aniline; and/or
   (b) the explosive compound is an organic compound comprising one or more nitro groups; and/or
   (c) the polycyclic aromatic hydrocarbon is selected from one or more of the group consisting of a fullerene, acenapthylene, pyrene, phenanthrene, fluorene, triphenylene, chrysene, naphthalene, and indene.

8. The method of claim 7, wherein the organic compound comprising one or more nitro groups is selected from one or more of the group consisting of nitrobenzene, nitromethane, 2-nitrotoluene, and 2,4,6-trinitophenol.

9. A sensor device comprising an optical fiber and the polymer of claim 1, having the repeating unit of formula (IV), optionally wherein the polymer is provided as a bulk polymer or as a nanosheet, where wherein the nanosheet has from one to four layers of the polymer.

10. A method of detecting a volatile organic compound and/or an explosive compound and/or a polycyclic aromatic hydrocarbon with the sensor device as recited in claim 9, comprising
    exposing the sensor device to an analyte to detect the volatile organic compound by turn-on fluorescence; or
    exposing the sensor device to an analyte to detect the explosive compound or the polycyclic aromatic hydrocarbon by turn-off fluorescence in a quantitative manner or in a qualitative manner, optionally wherein:
    (a) the volatile organic compound is selected from one or more of the group consisting of dichloromethane, chloroform, tetrahydrofuran, n-hexane, cyclohexane, benzene, toluene, o-xylene, m-xylene, p-xylene, 1,4-diisopropylbenzene, and aniline; and/or
    (b) the explosive compound is an organic compound comprising one or more nitro groups; and/or
    (c) the polycyclic aromatic hydrocarbon is selected from one or more of the group consisting of a fullerene, acenapthylene, pyrene, phenanthrene, fluorene, triphenylene, chrysene, naphthalene, and indene.

11. The method of claim 10, wherein the organic compound comprising one or more nitro groups is selected from one or more of the group consisting of nitrobenzene, nitromethane, 2-nitrotoluene, and 2,4,6-trinitophenol.

\* \* \* \* \*